US008756072B2

(12) United States Patent
Hussam

(10) Patent No.: US 8,756,072 B2
(45) Date of Patent: Jun. 17, 2014

(54) GENERATION AND DATA MANAGEMENT OF A MEDICAL STUDY USING INSTRUMENTS IN AN INTEGRATED MEDIA AND MEDICAL SYSTEM

(75) Inventor: Ali Adel Hussam, Columbia, MO (US)

(73) Assignee: Universal Research Solutions, LLC, Columbia, MO (US)

( * ) Notice: Subject to any disclaimer, the term of this patent is extended or adjusted under 35 U.S.C. 154(b) by 541 days.

(21) Appl. No.: 12/774,696

(22) Filed: May 5, 2010

(65) Prior Publication Data

US 2011/0093292 A1    Apr. 21, 2011

Related U.S. Application Data

(63) Continuation-in-part of application No. 12/699,522, filed on Feb. 3, 2010, and a continuation-in-part of application No. 12/699,655, filed on Feb. 3, 2010, and a continuation-in-part of application No. 12/699,673, filed on Feb. 3, 2010.

(60) Provisional application No. 61/253,398, filed on Oct. 20, 2009.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ......................................................... 705/2–3
See application file for complete search history.

(56) References Cited

U.S. PATENT DOCUMENTS

| 7,711,580 | B1* | 5/2010 | Hudson ............................. 705/3 |
| 2002/0035486 | A1 | 3/2002 | Huyn et al. |
| 2003/0028399 | A1* | 2/2003 | Davis et al. ....................... 705/2 |
| 2003/0208465 | A1 | 11/2003 | Yurko et al. |
| 2004/0059711 | A1 | 3/2004 | Jandel et al. |
| 2004/0059714 | A1 | 3/2004 | Laresen et al. |
| 2004/0153343 | A1 | 8/2004 | Gotlib et al. |
| 2004/0172293 | A1* | 9/2004 | Bruschi et al. .................... 705/2 |

(Continued)

OTHER PUBLICATIONS

PCT Notification of Transmittal of International Search Report and Written Opinion of the International Searching Authority in counterpart International Application No. PCT/US2010/053381, dated May 26, 2011.

(Continued)

*Primary Examiner* — Joseph Burgess
(74) *Attorney, Agent, or Firm* — Fish & Richardson P.C.

(57) ABSTRACT

In general, a computer-implemented method is described for receiving one or more requests to generate a medical study, retrieving from one or more data repositories one or more medical study instruments, receiving a selection of a particular medical study instrument to use in the medical study, generating by one or more computers a list of one or more research collaborators invited to review the medical study, and generating by one or more computers a list of one or more participants invited to join the medical study. Additionally, the computer-implemented method receives from a patient one or more responses to one or more medical assessment questions; and causes one or more computer systems to associate one or more medical study instruments with the patient, with the association based on the one or more responses of the patient to the one or more medical assessment questions.

19 Claims, 28 Drawing Sheets

(56) References Cited

U.S. PATENT DOCUMENTS

| | | |
|---|---|---|
| 2008/0010251 A1 | 1/2008 | Fontoura et al. |
| 2008/0010254 A1 | 1/2008 | Settimi |
| 2008/0059237 A1 | 3/2008 | Koren et al. |
| 2008/0097918 A1 | 4/2008 | Spector et al. |
| 2008/0172216 A1 | 7/2008 | Cramer et al. |
| 2008/0172246 A1 | 7/2008 | Larkin et al. |
| 2008/0215356 A1 | 9/2008 | Vancho |

OTHER PUBLICATIONS

PCT Notification of Transmittal of International Search Report and Written Opinion of the International Searching Authority in counterpart International Application No. PCT/US2010/053406, dated May 30, 2011.

PCT Notification Concerning Transmittal of International Preliminary Report on Patentability and Written Opinion of the International Searching Authority from International Application No. PCT/US2010/053406, dated May 3, 2012 (5 pages).

* cited by examiner

Survey Settings ▷ Questions ▷ Overview ▷ Test ▷ Score ▷ Validate ▷ Collaborate    Send to Subject

GENERAL

| | |
|---|---|
| Thread Title / Author —— 304 | Last Post |
| Additional Questions<br>Dr. Julie Goss —— 306 | 04.05.09<br>by Dr. Dan Mudd |
| Issues with Question 5<br>Dr. Julie Goss —— 308 | 7.06.09<br>by Dr. Tim Linder |
| Potential images<br>Dr. Tim Linder —— 310 | 01.22.09<br>by Dr. Tim Linder |
| Rollout Timeline<br>Dr. Julie Goss | 01.21.09<br>by Dr. Julie Goss |

(add)

This questionnaire asks about your symptoms as well as your ability to perform certain activities. Please answer every question based on your condition in the LAST WEEK. If you did not have the opportunity to perform an activity in the past week, please make your best estimate on which response would be the most accurate. It doesn't matter which hand or arm you use to perform the activity, please answer based on you ability regardless of how you perform the task.

302

Open a tight jar [Movie] — No Difficulty | Mild Difficulty | Moderate Difficulty | Severe Difficulty | Unable to complete Write — No Difficulty | Mild Difficulty | Moderate Difficulty | Severe Difficulty | Unable to complete Prepare a meal [Movie] — No Difficulty | Mild Difficulty | Moderate Difficulty | Severe Difficulty | Unable to complete Push open a heavy door [Movie] — No Difficulty | Mild Difficulty | Moderate Difficulty | Severe Difficulty | Unable to complete Use a knife to cut food — No Difficulty | Mild Difficulty | Moderate Difficulty | Severe Difficulty | Unable to complete (Back)                    (Next)

GENERATION AND DATA MANAGEMENT OF A MEDICAL STUDY USING INSTRUMENTS IN AN INTEGRATED MEDIA AND MEDICAL SYSTEM

CLAIM OF PRIORITY

This application is a continuation-in-part and claims priority under 35 U.S.C. §120 to U.S. patent application Ser. Nos. 12/699,522, filed on Feb. 3, 2010, Ser. No. 12/699,655, filed on Feb. 3, 2010, and Ser. No. 12/699,673, filed on Feb. 3, 2010, each of which in turn claim priority under 35 U.S.C. §119(e) to provisional U.S. Patent Application 61/253,398, filed on Oct. 20, 2009, the entire contents of each of which are hereby incorporated by reference.

BACKGROUND

Medical forms are used to collect data and information regarding a patient's symptoms and conditions. One technique for preparing a medical form is to manually edit a pre-existing form (e.g., a form existing in Microsoft Word™ format) with new or customized questions. The form is then sent to review boards for review through a physical or electronic mailing. Additionally, once a form has been finalized, it may be presented to a patient, study participant or other individual (collectively referred to as "patients" herein, without limitation, for purposes of convenience). For example, physicians may present patients with the forms when the patient visits the physician's office. Additionally, hardcopy (i.e., paper) versions of medical forms may be distributed to patients for completion. For patient's who have not completed medical forms prior to the patient's examination, the patient may often complete the medical form at the physician's office by filling out a hardcopy of the form.

Frequently, the patient's responses to the questions included in the medical forms are entered into a computerized system by medical personnel. In this case, in order for a physician to review the patient's responses, the physician may access the computerized system and view the answers to the questions, which is often a lengthy process of reviewing individual questions.

SUMMARY

The techniques described above fail to provide an integrated system for generating and validating an instrument (e.g., medical forms and questionnaires) and collecting data associated with the validated instrument, such that the data is more readily accessible to researchers for analysis.

In one exemplary embodiment, the techniques described herein provide, for example, an integrated system for physicians and other health care providers to generate instruments that are reviewed and validated through the use of threaded discussions and also to distribute the generated instruments to patients for completion. In another exemplary embodiment, the results of completed instruments are stored in a database that is integrated with the system and that is accessible to researchers and collaborators for review.

One aspect of the disclosure provides a computer-implemented method for receiving one or more requests to generate a medical study, retrieving from one or more data repositories one or more medical study instruments, receiving a selection of a particular medical study instrument to use in the medical study, generating by one or more computers a list of one or more research collaborators invited to review the medical study, and generating by one or more computers a list of one of more participants invited to join the medical study.

Implementations of the disclosure may include one or more of the following features. In some implementations, the method includes generating a graphical user interface that when rendered on a display device renders a visual representation of a timeline, indicating, for one or more questions included in the selected medical study instrument, a question completion date. The method may also include generating by one or more computers a customized medical study instrument by: receiving one or more request messages indicating a type of question to be included in the customized medical study instrument, question text to be included in the customized medical study instrument and one or more answers to be included in the customized medical study instrument and associated with the question text.

In some implementations, the method includes linking a score value to one or more questions included in the customized medical study instrument, and generating a scoring rule based on the linked score values. The method may also include generating a notification messaging indicating that one or more questions included in the medical study instrument need to be answered, and sending the notification message to one or more participants of the medical study.

In other implementations, the method includes generating a graphical user interface that when rendered on a display device renders a visual representation of a dashboard comprising one or more real-time indicators of the medical study's progress, instrument scoring, patient enrollment, timelines and patient reminders. The method may also include generating by one or more computers a graphical user interface that when rendered on a display device renders a visual representation of a forum for review of the medical study instrument, the visual representation of the forum comprising: one or more text boxes for reviewers to enter text, the text boxes associated with one or more questions included in the medical study instrument, and a link between the one or more text boxes and an associated question, selection of the link causing the associated question to be rendered on the display device.

In yet other implementations, the method includes generating by one or more computers a multimedia module to explain one or more features of a particular question, and generating a link between the particular question and the multimedia module. The method may also include receiving by one or more computers one or more responses to questions included in the medical study instrument, retrieving by one or more computers one or more scoring rules, and executing by one or more computers the one or more scoring rules to determine a score of the received responses.

Another aspect of the disclosure provides a computer program product residing on a computer readable storage medium, the computer program product comprising instructions for causing a computer to: receive one or more requests to generate a medical study, retrieve from one or more data repositories one or more medical study instruments, receive a selection of a particular medical study instrument to use in the medical study, generate a list of one or more research collaborators invited to review the medical study, and generate a list of one of more participants invited to join the medical study.

Implementations of the disclosure may include one or more of the following features. In some implementations, the computer program product includes instructions for causing the computer to generate a graphical user interface that when rendered on a display device renders a visual representation of a timeline, indicating, for one or more questions included in the selected medical study instrument, a question completion date. The computer program product may also include instructions for causing the computer to generate a customized medical study instrument by: receiving one or more request messages indicating a type of question to be included in the customized medical study instrument, question text to be included in the customized medical study instrument and one or more answers to be included in the customized medical study instrument and associated with the question text.

In other implementations, the computer program product includes instructions for causing the computer to link a score value to one or more questions included in the customized medical study instrument, and generate a scoring rule based on the linked score values. The computer program product may also include instructions for causing the computer to generate a notification messaging indicating that one or more questions included in the medical study instrument need to be answered, and send the notification message to one or more participants of the medical study.

In yet other implementations, the computer program product includes instructions for causing the computer to generate a graphical user interface that when rendered on a display device renders a visual representation of a dashboard comprising one or more real-time indicators of the medical study's progress, instrument scoring, patient enrollment, timelines and patient reminders. The computer program product may also include instructions for causing the computer to generate a graphical user interface that when rendered on a display device renders a visual representation of a forum for review of the medical study instrument, the visual representation of the forum comprising: one or more text boxes for reviewers to enter text, the text boxes associated with one or more questions included in the medical study instrument, and a link between the one or more text boxes and an associated question, selection of the link causing the associated question to be rendered on the display device. The computer program product may also include instructions for causing the computer to generate a multimedia module to explain one or more features of a particular question; and generate a link between the particular question and the multimedia module.

In still other implementations, the computer program product includes instructions for causing the computer to receive one or more responses to questions included in the medical study instrument, retrieve one or more scoring rules, and execute the one or more scoring rules to determine a score of the received responses.

Another aspect of the disclosure provides an apparatus comprising: a processor; and a computer program product residing on a computer readable storage medium, the computer program product comprising instructions for causing the processor to: receive one or more requests to generate a medical study; retrieve from one or more data repositories one or more medical study instruments; receive a selection of a particular medical study instrument to use in the medical study; generate a list of one or more research collaborators invited to review the medical study; and generate a list of one of more participants invited to join the medical study.

Implementations of the disclosure may include one or more of the following features. In some implementations, the computer program product includes instructions for causing the computer to perform the features described above, for example, instructions for causing the computer to generate a graphical user interface that when rendered on a display device renders a visual representation of a timeline, indicating, for one or more questions included in the selected medical study instrument, a question completion date.

Another aspect of the disclosure provides a computer-implemented method for retrieving by one or more computers one or more answer options to an associated question included in a medical study, with one or more of the answer options linked to a color value indicative of a disability level associated with a medical issue, causing one or more computers to determine for the one or more answer options a display color for the answer option according to the color value, and generating by one or more computers a graphical user interface that when rendered on a display device renders a first visual representation of the one or more answer options in the determined display color, the one or more answer options juxtaposed to a second visual representation of the associated question.

One aspect of the disclosure provides a computer-implemented method for receiving from a patient, through one or more computer systems, one or more responses to one or more medical assessment questions; and causing the one or more computer systems to associate one or more medical study instruments with the patient, with the association based on the one or more responses of the patient to the one or more medical assessment questions.

Implementations of the disclosure may include one or more of the following features. In some implementations, the method includes generating one or more instrument selection rules, with the one or more instrument selection rules indicating a correspondence between the one or more responses to the one or more medical assessment questions and the one or more medical study instruments. The method may also include causing the one or more computer systems to apply the one or more instrument selection rules to the one or more responses to the one or more medical assessment questions; and generating, based on the application of the one or more instrument selection rules to the one or more responses, a list of one or more medical study instruments to be associated with the patient.

Another aspect of the disclosure provides a computer-implemented method for generating by one or more computer systems a summary of a patient's medical data; receiving, from a health care professional, a confirmation message, the confirmation message comprising data indicating that the health care professional has reviewed one or more medical items included in a summary of the patient's medical data; and causing the one or more computer systems to update a database record of a patient in a database with information indicating that the health care professional has reviewed one or more of the medical items.

Implementations of the disclosure may include one or more of the following features. In some implementations, the health care professional includes a first health care professional and the method may also include receiving from the first health care professional one or more update messages, the one or more update messages comprising medical data for the patient; updating the record of the patient in the database with the medical data included in the one or more update messages; and generating a graphical user interface that when rendered on a display device renders a visual representation of the updated record of the patient, with a confirmation link juxtaposed to the visual representation, selection of the confirmation link causing the record of the patient to be updated with information indicating that a second health care professional has reviewed and confirmed the updated record of the patient.

In other implementations, the health care professional includes a first health care professional and the method includes causing the one or more computer systems to update the database record of the patient with information indicating that a second health care professional has reviewed the one or more medical items. The method also includes retrieving from the one or more computer systems the one or more medical assessment questions and causing the one or more computer systems to associate a pointer with the received confirmation message, with execution of the pointer causing the database record of the patient to be updated with the information that the health care professional has reviewed one of more of the medical items and the reviewed one of more medical items are accurate.

Another aspect of the disclosure provides a computer program product embodied on a computer readable storage medium, the computer program product including instructions for causing a computer to: receive, from a patient, one or more responses to one or more medical assessment questions; and associate one or more medical study instruments with the patient, with the association based on the one or more responses of the patient to the one or more medical assessment questions.

Implementations of the disclosure may include one or more of the following features. In some implementations, the computer program product further includes instructions for causing the computer to: generate one or more instrument selection rules, with the one or more instrument selection rules indicating a correspondence between the one or more responses to the one or more medical assessment questions and the one or more medical study instruments. The computer program product may also include instructions for causing the computer to: apply the one or more instrument selection rules to the one or more responses to the one or more medical assessment questions; and generate, based on the application of the one or more instrument selection rules to the one or more responses, a list of one or more medical study instruments to be associated with the patient.

Another aspect of the disclosure provides computer program product embodied on a computer readable storage medium, the computer program product including instructions for causing a computer to: generate a summary of a patient's medical data; receive, from a health care professional, a confirmation message, the confirmation message comprising data indicating that the health care professional has reviewed one or more medical items included in a summary of the patient's medical data; and update a database record of a patient in a database with information indicating that the health care professional has reviewed one or more of the medical items.

Implementations of the disclosure may include one or more of the following features. In some implementations, the health care professional includes a first health care professional and the computer program product further includes instructions for causing the computer to: receive from the first health care professional one or more update messages, the one or more update messages comprising medical data for the patient; update the record of the patient in the database with the medical data included in the one or more update messages; and generate a graphical user interface that when rendered on a display device renders a visual representation of the updated record of the patient, with a confirmation link juxtaposed to the visual representation, selection of the confirmation link causing the record of the patient to be updated with information indicating that a second health care professional has reviewed and confirmed the updated record of the patient.

In other implementations, the health care professional includes a first health care professional and the computer program product further includes instructions for causing the computer to: update the database record of the patient with information indicating that a second health care professional has reviewed the one or more medical items.

Another aspect of the disclosure provides an apparatus comprising: a processor; and a computer program product embodied on a computer readable storage medium, the computer program product including instructions for causing the processor to: receive, from a patient, one or more responses to one or more medical assessment questions; and associate one or more medical study instruments with the patient, with the association based on the one or more responses of the patient to the one or more medical assessment questions.

Implementations of the disclosure may include one or more of the following features. In some implementations, the computer program product of the apparatus further includes instructions for causing the computer to: generate one or more instrument selection rules, with the one or more instrument selection rules indicating a correspondence between the one or more responses to the one or more medical assessment questions and the one or more medical study instruments. The computer program product of the apparatus may also include instructions for causing the computer to: apply the one or more instrument selection rules to the one or more responses to the one or more medical assessment questions; and generate, based on the application of the one or more instrument selection rules to the one or more responses, a list of one or more medical study instruments to be associated with the patient.

Another aspect of the disclosure provides an apparatus comprising a processor; and a computer program product embodied on a computer readable storage medium, the computer program product including instructions for causing the processor to: generate a summary of a patient's medical data; receive, from a health care professional, a confirmation message, the confirmation message comprising data indicating that the health care professional has reviewed one or more medical items included in a summary of the patient's medical data; and update a database record of a patient in a database with information indicating that the health care professional has reviewed one or more of the medical items.

Implementations of the disclosure may include one or more of the following features. In some implementations, the health care professional includes a first health care professional and the computer program product of the apparatus further includes instructions for causing the computer to: receive from the first health care professional one or more update messages, the one or more update messages comprising medical data for the patient; update the record of the patient in the database with the medical data included in the one or more update messages; and generate a graphical user interface that when rendered on a display device renders a visual representation of the updated record of the patient, with a confirmation link juxtaposed to the visual representation, selection of the confirmation link causing the record of the patient to be updated with information indicating that a second health care professional has reviewed and confirmed the updated record of the patient.

In other implementations, the health care professional includes a first health care professional and the computer program product of the apparatus further includes instructions for causing the computer to: update the database record of the patient with information indicating that a second health care professional has reviewed the one or more medical items.

BRIEF DESCRIPTION OF THE FIGURES

FIGS. 4-6, 8-14, 16-18 and 23-27 are screen images of a graphical user interface generated by the medical integration system.

DETAILED DESCRIPTION

Overview

The system described herein provides, for example, an integrated information and communication platform for outcome and evidence-based medical research. Using the system, researchers may design studies to test the efficacy of medical devices, medical instruments and medical treatments. Through the system, researchers may also collaborate with colleagues to validate and to refine the study and invite patients to participate in the study. Patients may further access the study through the system.

In the exemplary embodiment described herein, through the use of portal systems and dashboards, researchers have access to the progress of a study and real-time feedback from the participants of the study. The described system collects data from the study and stores it in a database accessible to patients, physicians, nurses, health care providers, experts, researchers, reviewers and other individuals (collectively referred to as "users" herein, without limitation, for purposes of convenience) of the system, thereby enabling worldwide collaborative research. As data is collected from the study, the exemplary system provides research analysis tools that enable users of the system to quantify outcome of a treatment under study by performing, for example, Rasch analysis, factor analysis, model testing, and a variety of statistical analysis to assess reliability, scaling and scoring of the results of the study. The exemplary system also includes data mining tools to detect patterns in the collected data and convert continuous data into discrete categories of data.

Figure 1:
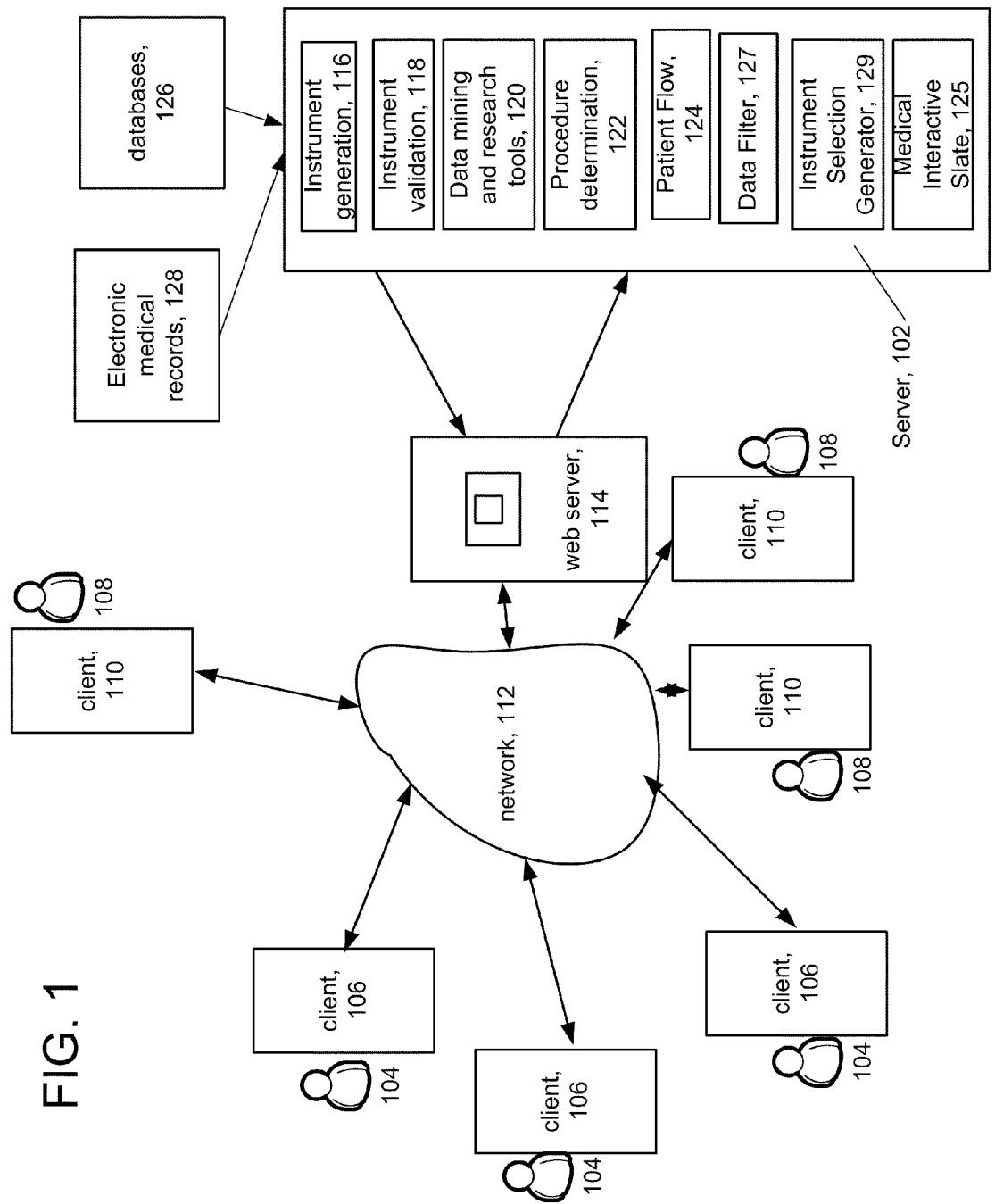
FIG. 1 is a diagrammatic view of a system for generating and tracking medical study instruments.

FIG. 1 illustrates a particular exemplary embodiment described herein. Referring to FIG. 1, the illustrated network computer system 100 includes a medical integration system (e.g., a server) 102 for making connections with users of the system 100, including patients 104, at client systems 106, and health care professionals (e.g., physicians, medical clinic staff, research collaborators and research review boards) 108, at client systems 110. In a preferred embodiment, the system may operate over a network 112, e.g., the Internet or other types of networks. The medical integration system 102 operates as a service running on, for example, a web server 114. In this embodiment, users 104, 108 of the system 100 may connect to the medical integration system 102 through a website or graphical user interface on the web server 114 using client systems 106, 110.

Client systems 106, 110 include, for example, mobile devices (e.g., cellular and mobile telephones, Blackberries™, iPhones™ and personal digital assistants), personal computing devices (e.g., laptop and desktop computers and iPads™), dedicated computing devices (e.g., kiosk systems installed in a doctor's office or medical clinic), and media-player-type devices. Client systems 110 also include furniture equipped with a computing device. In a particular example, a chair in a physician's office includes a mounted personal computing device (e.g., a laptop connected to the arm rest of a chair) through which users access the medical integration system 102 over the network 112. In this example, because numerous patients use the personal computing device, an ultraviolet ("UV") light may be included in the personal computing device and cast on the keyboard of the personal computing device to remove and destroy germs located on the personal computing device.

The illustrated medical integration system 102 includes an instrument generation module 116, an instrument validation module 118, a data mining and research tools module 120, a procedure determination module 122, and a patient flow module 124. Through a communication channel, including for example and without limitation a connection, a buffer or a path between various nodes in a network, the medical integration system 102 may also access one or more databases 126 and one or more electronic medical record ("EMR") systems 128 to import data (e.g., medical data from external and/or internal data sources) into the medical integration system 102. The components and modules 116, 118, 120, 122 and 124 of the medical integration system 102 and the web server 114 may be integrated or distributed in various combinations as is commonly known in the art.

Instrument Generation Module

In the exemplary embodiment described herein, users may generate study instruments (e.g., forms and questionnaires) for studies (e.g., medical studies) through the instrument generation module 116 of the medical integration system 102. In a preferred embodiment, an instrument generation system includes an instrument generation module.

The instrument generation module 116 enables a user to define various features of a study, including a study description, a list of instruments used in the study, a study and/or instrument timeline, invitations for doctors to participate in the study, and a checklist of criteria for a patient to posses for inclusion in the study. The instruments may include pre-defined forms and questionnaires stored in the medical integration system 102, and forms and questionnaires custom designed for a particular study. The pre-defined instruments can be augmented through the association of additional data, including lab tests and observations provided by physicians, nurses, care givers, or family members.

Figure 2:
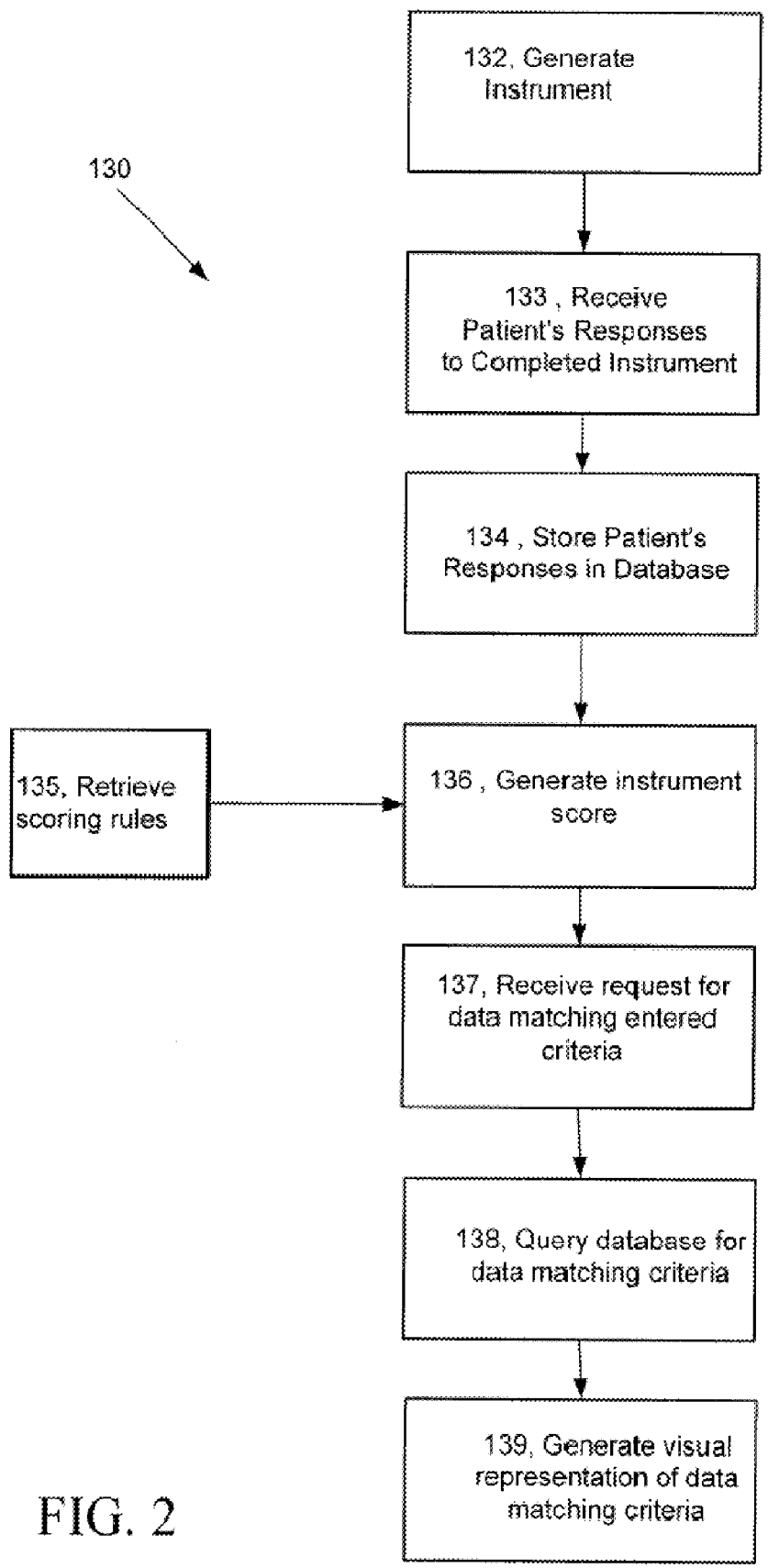
FIGS. 2, 3, 7, 15 and 19-22 are flowcharts of processes used by a medical integration system.

FIG. 2 illustrates a particular exemplary embodiment described herein. Referring to FIG. 2, the medical integration system 102 executes 130 and combines various processes including the following. In this exemplary embodiment, the medical integration system 102 generates 132 an instrument, as described in further detail below. The medical integration system 102 also receives 133 patients' responses to competed instruments and stores 134 the patients' responses in the database 126. A scoring system including scoring rules defines how a patient's responses to answers in an instrument are valued or "scored," as described in further detail below. The medical integration system 102 retrieves 135 from the database 126 one or more scoring rules and generates 136 an instrument score by applying the scoring rules to the answers associated with an instrument.

In this embodiment, the medical integration system 102 performs data analysis on the stored patient responses and generates visual representations of the data analysis which is presented to users of the medical integration system 102 through a graphical user interface. The medical integration system 102 receives 137 a request from a user for data matching criteria that the user has entered. The medical integration system 102 generates, for example, a query based on the entered criteria and queries 138 the database 126 for data matching the entered criteria included in the query, as described in further detail below. The medical integration system 102 also generates 139 a visual representation of the data matching the entered criteria.

Figure 3:
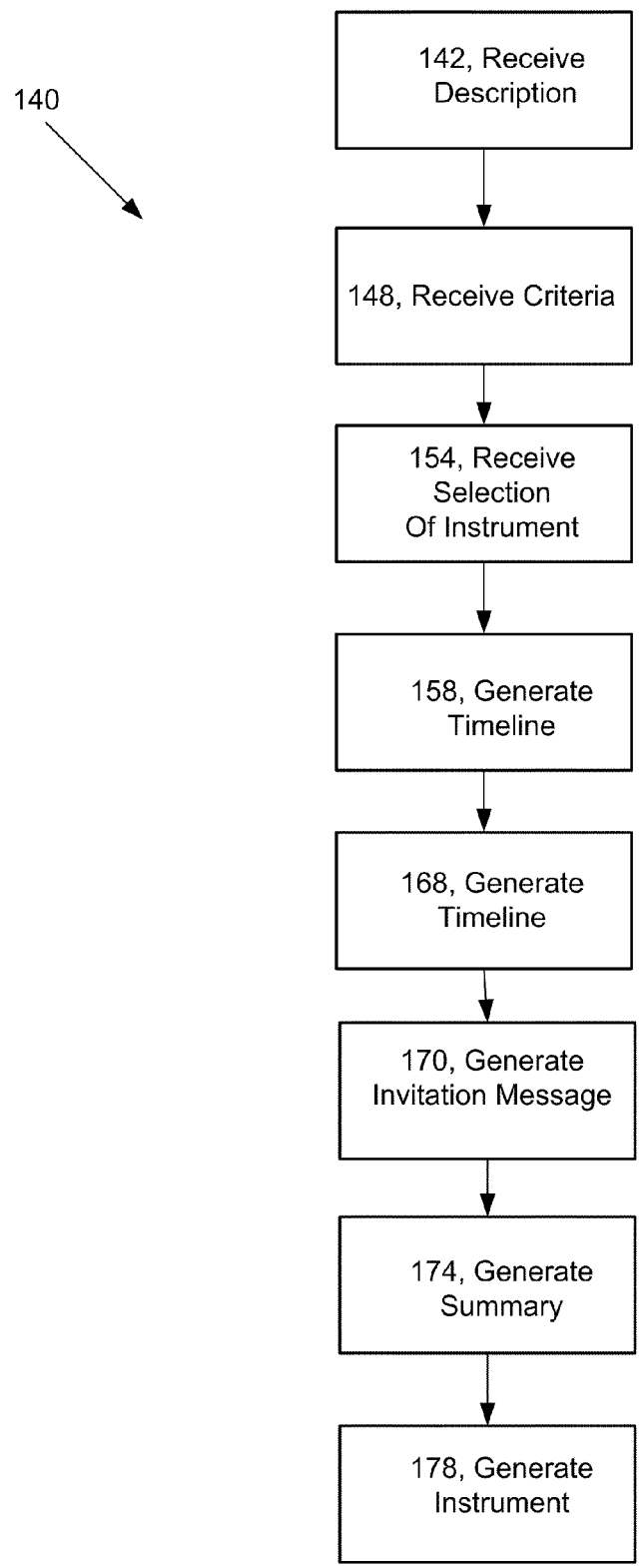
Figure 4:
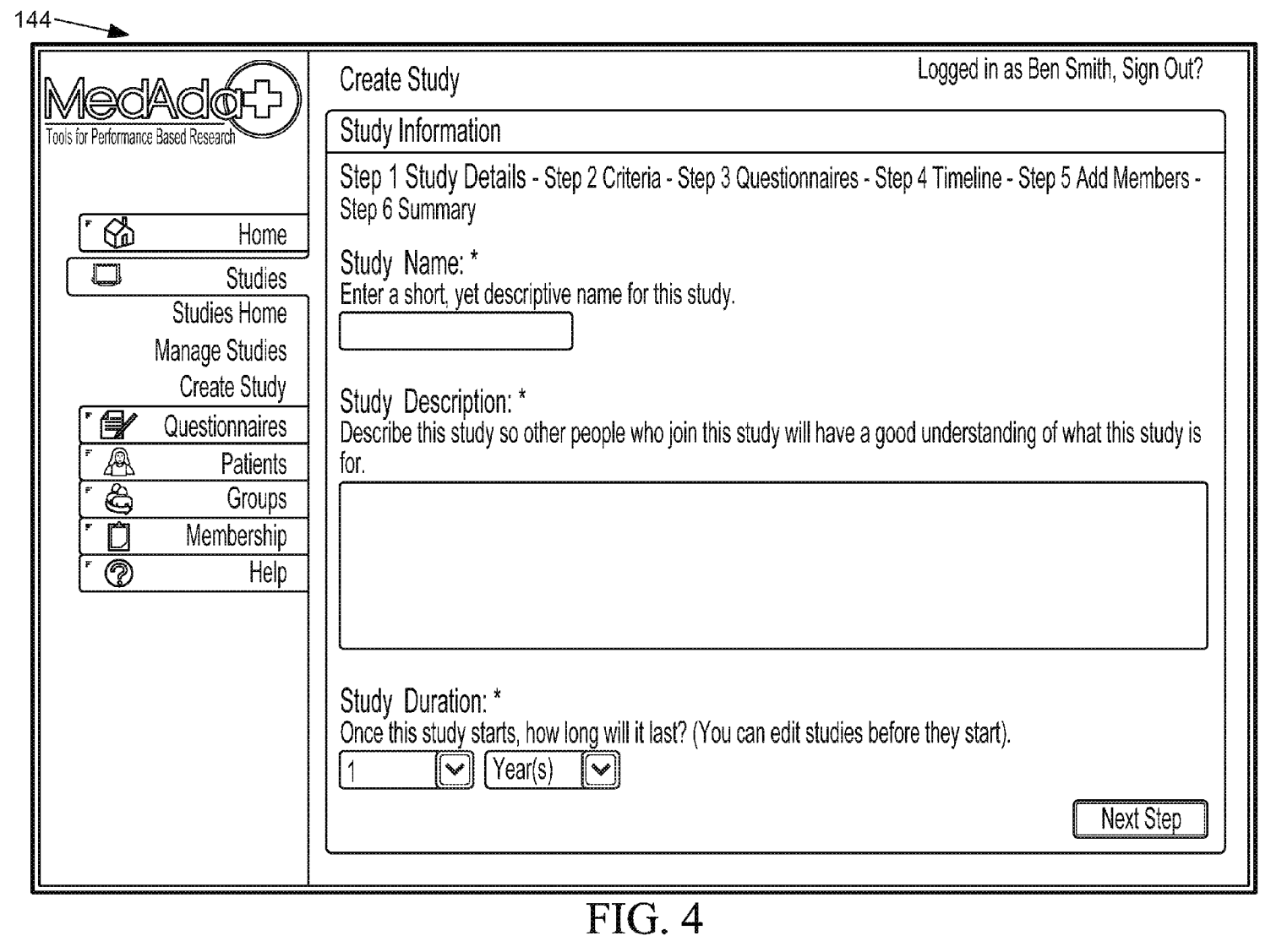

FIG. 3 illustrates a particular exemplary embodiment described herein. Referring to FIG. 3, the medical integration system 102 generates 140 a study instrument, as follows. The medical integration system 102 receives 142 a description of the study entered into the system 102 through a graphical user interface 144, an example of which is illustrated in FIG. 4. The description of the study may include study details (e.g., information about a study), the name of the study, study duration (e.g., a length in time which the study is available for a patient to complete), a number of patients to be included in the study, and clinic accessibility information (e.g., whether physicians within a clinic are granted permissions to view a study).

Figure 5:

In this embodiment, the medical integration system 102 receives 148 various criteria for a patient to possess in order to be included in the study. The system 102 may generate a graphical user interface 150, an example of which is illustrated in FIG. 5. Through the graphical user interface 150, the user may enter various patient criteria, including diagnosis codes, International Statistical Classification of Diseases and Related Health Problems ("ICD") codes (e.g., ICD-9 and ICD-10 codes), Current Procedural Terminology ("CPT") codes and other various diagnosis information and treatment information and various inclusive or exclusive criteria (e.g., age information, height information, weight information and smoker status information). The system 102 includes, for example, a utility to search an ICD code library based on an ICD code description or a partial ICD code to find the correct code. Additionally, the system 102 may generate a list of predefined criteria and displays this generated list for the user during generation of the instrument.

In the exemplary embodiment described herein and referring back to FIG. 3, the medical integration system 102 receives 154 a selection of one or more instruments to be used in the study. The instruments include pre-defined forms, which may be standard for a particular industry, for example the medical industry. The instruments may also be custom generated, as described in further detail below. The medical integration system 102 generates 158 an instrument timeline, which specifies the time (e.g., a number of days, weeks or months) in which a particular question in the instrument should be answered by a patient participating in the study. The timeline may also include the amount of time an instrument is made available to the user to complete.

Figure 6:
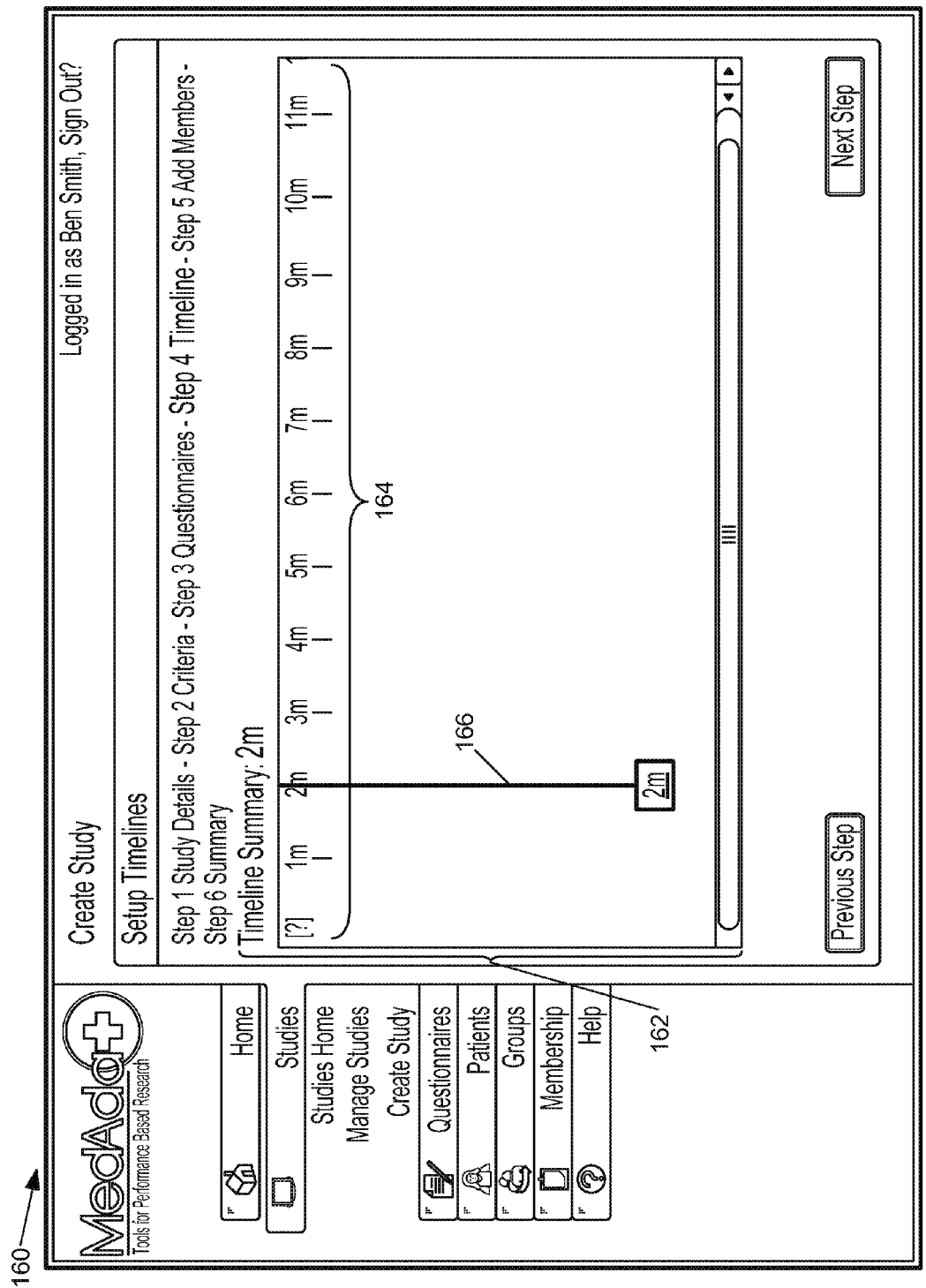

FIG. 6 illustrates a particular exemplary embodiment described herein. Referring to FIG. 6, the medical integration system 102 generates a graphical user interface 160 through which the timeline 162 may be displayed. In this embodiment, the illustrated timeline 162 includes a horizontal axis 164 specifying a number of months relative to the start date of the study for which a particular question should be completed by a patient. The illustrated timeline 162 may also include a vertical link 166, which is capable of moving along the horizontal axis 164 to select a particular month (e.g., two months or four months) in which a particular question should be completed by a patient. As user herein and throughout the application, the term "link" includes, without limitation, pointers, Uniform Resource Location links, a reference or pointer to physical data, and a file that serves as a reference to another file.

In the exemplary embodiment described herein and referring back to FIG. 2, the medical integration system 102 generates 170 invitation messages inviting physicians to join a study. The system 102 may include an invitation module, through which users invite physicians and other health care providers (collectively referred to as "physicians" herein, without limitation, for purposes of convenience) to participate in the study and to enroll their respective patients in the study. The invitation module generates, for example, a list of physicians associated with the user's hospital, clinic and/or research facility. The invitation module may also generate a list of physicians who have previously participated in studies generated by the medical integration system 102.

Through the invitation module, the user may select from the generated lists physicians to invite to join the study. To find physicians to invite to join the study, the user may also search the system 102 for the names of individual physicians to participate in and to collaborate in the study. In addition to inviting individual physicians, the user may define groups of physicians to participate in the study as collaborators, observers, and students of the instrument. In this embodiment, the medical integration system 102 stores the names of groups of physicians that have previously been defined and invited to join other studies. The medical integration system 102 allows the user to access and search these pre-defined groups of physicians and invite groups of physicians to join the user's study. Through the invitation module, a user may also invite a physician not currently enrolled in the system 102 to participate in the study. In this preferred embodiment, the invitation module sends an invitation message (e.g., an email or other electronic message) to join the study to the invited physicians.

In this exemplary embodiment, the medical integration system 102 generates 174 a study summary, including the information (e.g., study description information, patient criteria information, selected questionnaire information, timeline information, and invited physician information) input into the medical integration system 102 by the user. The system 102 may receive from the user a verification message indicating that the summary information is accurate. The medical integration system 102 generates 178 the instrument and sends the invited physicians a copy of the instrument and a list of the user specified patient criteria. The medical integration system 102 may also record the completion date by which specific questions in the instrument should be answered according to the timeline 162. The medical integration system 102 may also send alert messages (e.g., electronic messages, text messages or short message service ("SMS") messages) of the upcoming completion dates to the participating patients.

In an exemplary embodiment, the medical integration system 102 also allows the user to specify whether "skipped questions" are allowed for the instrument and/or the number of questions to be completed before an instrument score is calculated. In a particular example, the user may specify whether the instrument allows a percentage of questions to be skipped or whether all questions in the instrument need to be completed.

Frequently, Internal Review Boards ("IRBs") require a patient to fill out a consent form prior to participating in a study or completing an instrument. For this case, the medical integration system 102 includes a consent form module through which users upload one or multiple consent forms to be presented to the patient before participating in the study and/or before starting an instrument.

In an exemplary embodiment, once a generated instrument has been finalized, the medical integration system 102 provides the user with the options to start the study or to leave the study open for editing and trial runs. When the study is left open for trial runs and editing, for example, the medical integration system 102 may generate an online forum for collaboration between the study generator and other participating users. Additionally, in this example when the study is left open for trial runs and editing, the study instrument is editable, meaning that the criteria and the study options described above are editable. If the user selects the option to start the study, the system 102 may send the selected patients, participants and collaborators an invitation message to view and participate in the study by completing the instrument.

In another exemplary embodiment, a study may include a customized instrument generated through the medical integration system 102. Users are provided a secure space to generate medically-based questions originating from various question styles used by standard instruments. Multimedia modules may be attached to the questions to make the questions more understandable for the patients completing the instrument.

Figure 7:
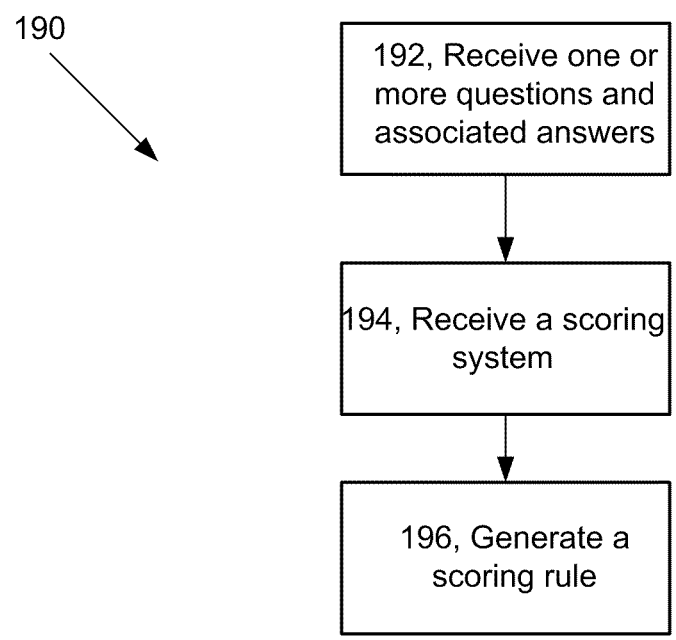

FIG. 7 illustrates a particular exemplary embodiment described herein. Referring to FIG. 7, the medical integration system 102 generates 190 a customized instrument, as follows. In this illustrated example, the medical integration system 102 receives 192 one or more questions and associated answers from a user. The medical integration system 102 also receives 194 from the user a scoring system associated with the questions and answers. The scoring system assigns a score value to each of the answers associated with a question, enabling a physician or researcher to assess the study results. The medical integration system 102 generates 196 scoring rules based on the numerical scores associated with answers. In some examples, the scoring rules add the numerical scores associated with completed answers. In this illustrated example, the scoring rules may calculate a weighted average for the numerical scores associated with the completed answers by assigning the questions a weighted value indicating the importance of the question relative to other questions. The medical integration system 102 prompts the user generating an instrument with a series of questions to determine the desired type of score system and may generate a cautionary notification if the user later applies an analytical procedure inappropriate for the selected score system (e.g., average age of study participants may be valid and important to a study, but average social security number is neither valid nor important to the study).

In generating a customized instrument, a user may select a type of question from a list of question types generated by the system 102. The types of questions include, for example, multiple-choice questions (e.g., one question with multiple number responses), a "Yes/No" question (e.g., one question with "Yes" or "No" as responses), a "True/False" question (e.g., one question with "True" or "False" as responses), a scaling question (e.g., one question and a sliding scale bar through which a user selects an answer located between two values, N1 and N2), an avatar/diagram question (e.g., an interactive question in which the user selects various sections of an image or freely draws on various sections of the image), a free response question in which a user inputs a predetermined amount of characters into a multi-line textbox (e.g., "describe in 1000 characters or less your symptoms").

Figure 8:
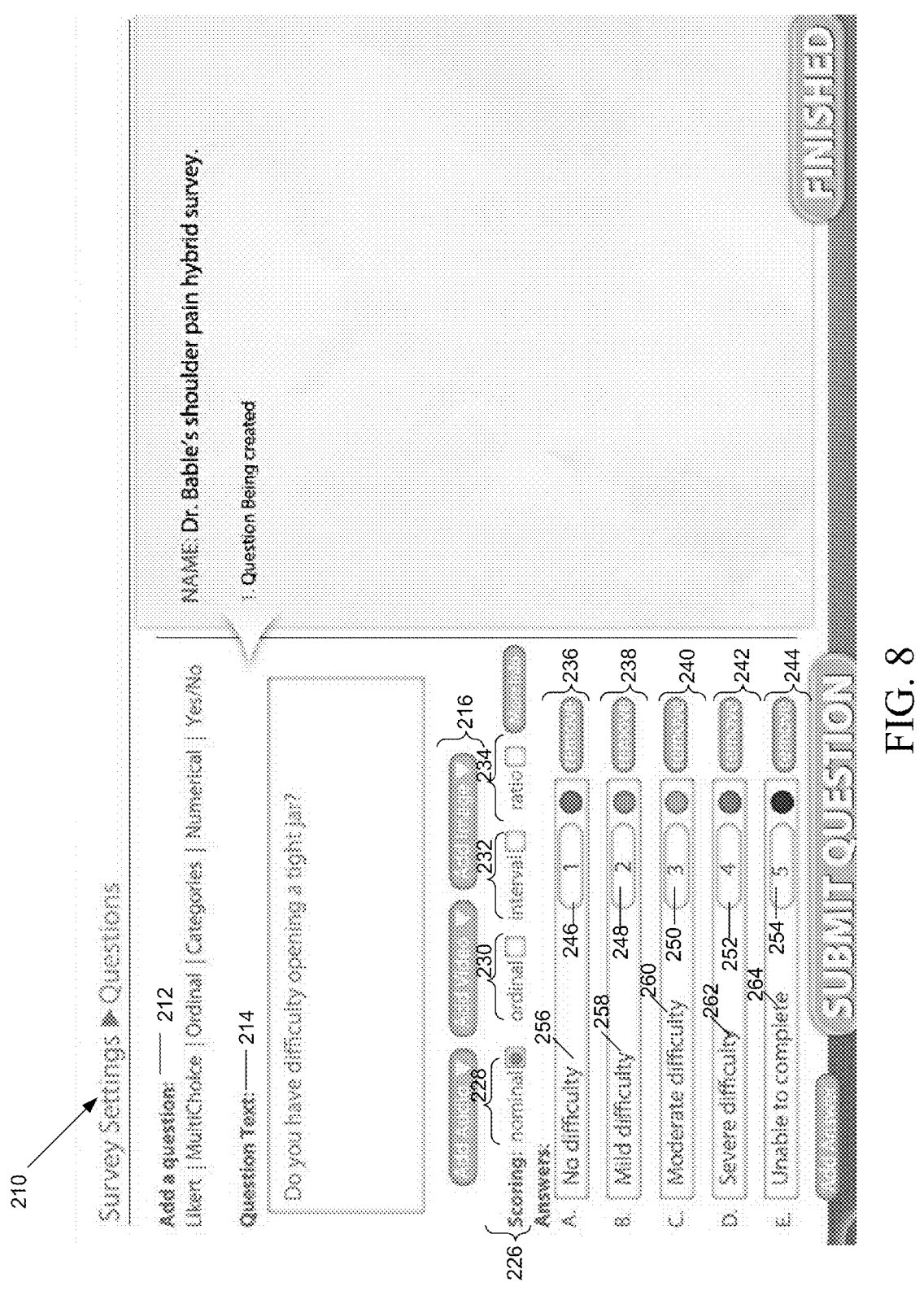

FIG. 8 illustrates a particular exemplary embodiment described herein. Referring to FIG. 8, the medical integration system 102 generates a graphical user interface 210 for a user to define custom questions for an instrument. In section 212 of the illustrated graphical user interface 210, the user may select the type of question to be added to the instrument. In this particular embodiment, the user enters question text (e.g., "do you have difficulty opening a tight jar?") in section 214 of the illustrated graphical user interface 210. In section 216 of the illustrated graphical user interface 210, the user is provided the option of adding a multimedia module (e.g., an image, an audio file or an image) to the question to assist a patient in understanding or interpreting the question. In this particular embodiment, the system 102 receives from the user's client system 106 request messages including data indicative of custom questions to be included in the instrument.

Figure 9:

FIG. 9 illustrates a particular exemplary embodiment described herein. Referring to FIG. 9, a multimedia module 220 may be linked to a question. In this particular embodiment, the illustrated multimedia module 220 includes a visual image 222 and an accompanying audio file 224.

Referring back to the illustrated example of FIG. 8, section 226 of the illustrated graphical user interface 210 allows the user to associate the question with a numerical score (i.e., numbers) and a score system, including, for example, a nominal system 228, an ordinal system 230, an interval system 232 and a ratio system 234. In a nominal score system, numerical identifiers are associated with a response (e.g., 1=blue, 2=red or 1=red, 2=blue). In an ordinal score system, the numerical scores are ordered in a meaningful way (e.g., 1=no pain, 2=some pain, 3=severe pain). In an interval score system, the difference between numerical scores is significant (e.g., a 20 degree temperature difference between answers relating to temperate correlates with a fixed amount of heat). In a ratio score system, the numerical scores represent a quotient, with the quotient indicative of the relative importance of an answer.

Numerical scores may be associated with question responses to facilitate scoring of an instrument and mathematical and/or statistical analysis. Frequently, studies are designed to test the efficacy of a medical procedure, treatment or device. Accordingly, in a preferred embodiment, numerical scores are associated with questions, where a higher numerical score indicates that the treatment is effective and a lower numerical score indicates that the treatment is not effective or is less effective. In this embodiment, an instrument includes the following question: "Did you experience an improvement in your symptoms following the treatment?" Answers associated with this question include, for example, a "Yes" answer, a "Moderately" answer, and a "No" answer. A numerical score of "3" is associated with the "Yes" answer. A numerical score of "2" is associated with the "Moderately" answer. A numerical score of "1" is associated with the "No" answer. In the illustrated example of FIG. 8, the answers 236, 238, 240, 242, 244 associated with a question are assigned a numerical score 246, 248, 250, 252, 254 based on the selected score system 228, 230, 232, 234. Additionally, in this example, a text box 256, 258, 260, 262 and 264 is provided in which the user enters text corresponding to the answers associated with the question.

In the exemplary embodiment described herein, the answers to questions may be associated with a color value indicative of a feature of the answer (e.g., answers directed toward a level of pain experienced by a patient or a level of difficulty the patient experiences in performing an activity). When the medical integration system 102 generates visual representations of the answers to a question, the visual representations may be color coded based on the color value associated with an answer.

Figure 10:
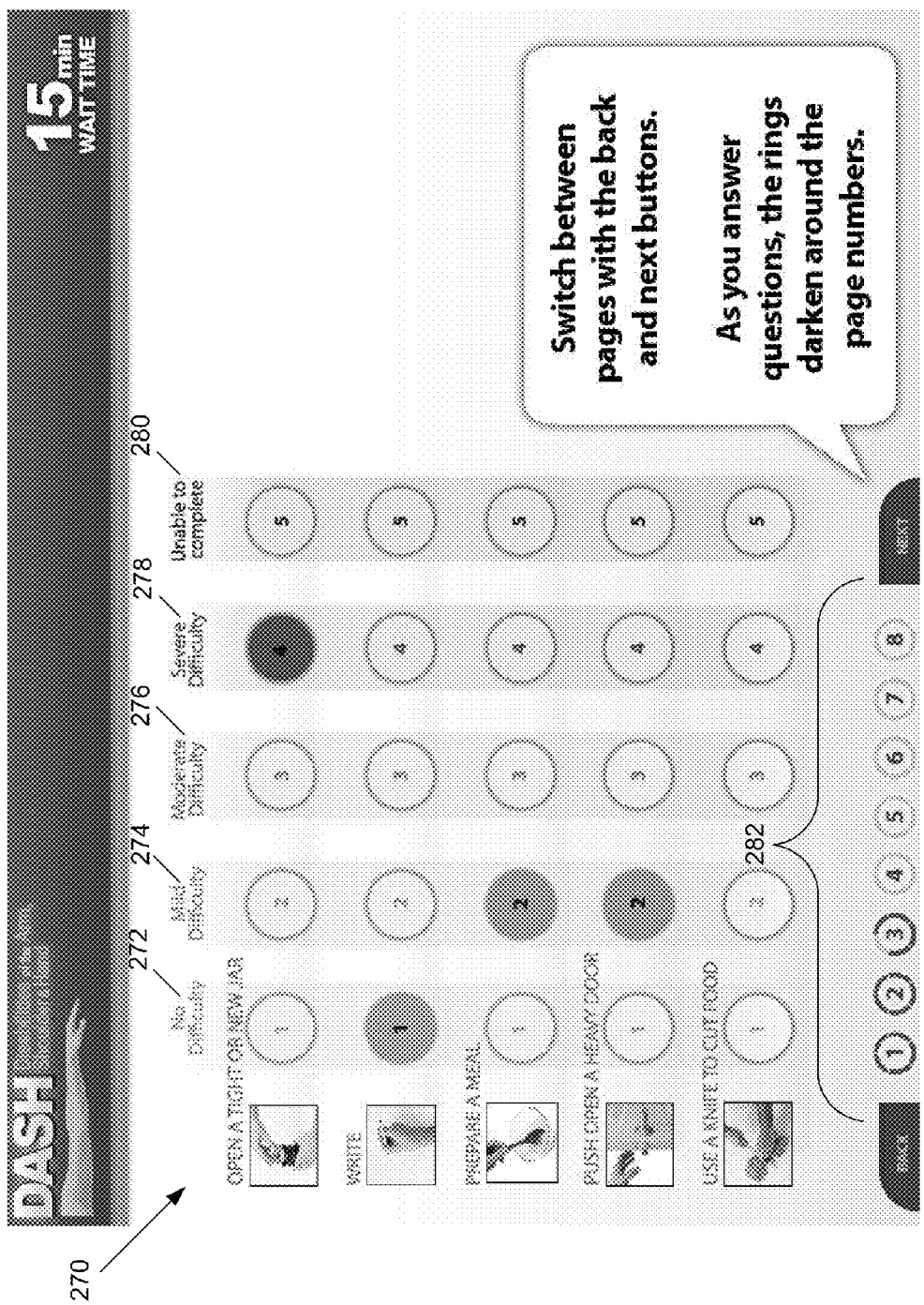

FIG. 10 illustrates a particular exemplary embodiment described herein. Referring to FIG. 10, the medical integration system 102 generates a graphical user interface 270 including, for example, answers to multiple questions. In this embodiment, the "no difficulty" column 272 of answers is color coded green. The "mild difficulty" column 274 of answers is color coded yellow. The "moderate difficulty" column 276 of answers is color coded orange. The "severe difficulty" column 278 of answers is color coded light red. The "unable to complete" column 280 of answers is color coded bright red.

A color value system may be executed by the medical integration system 102 in generating the illustrated graphical user interface 270 with the various colored columns of answers 272, 274, 276, 278, 280 according to the following color value rules, for example. Answers with a color value of "1" are assigned a color code of green, indicating that the physical action (e.g., preparing a meal) specified by the question is easy for the patient to perform. Answers with a color value of "2" are assigned a color code of yellow, indicating that the physical action specified by the question is mildly difficult for the patient to perform. Answers with a color value of "3" are assigned a color code of orange, indicating that the physical action specified by the question is moderately difficult for the patient to perform. Answers with a color value of "4" are assigned a color code of light red, indicating that the physical action specified by the question is severely difficult for the patient to perform. Answers with a color value of "5" are assigned a color code of bright red, indicating that the patient is not able to perform the physical action specified by the question.

In the exemplary embodiment described herein, an instrument includes various sections. A section includes, for example, its own set of instructions that pertain to a grouping of questions. A section also includes one or more associated questions. The types of instruments include patient instruments and physician instruments. Patient instruments are designed to be filled out by or on the behalf of a patient. Physician instruments are designed to be filled out by or on behalf of a physician in regards to a patient. Instruments may be translatable to the primary language of the user and are translatable in real time, based on a selected language of the user. Through an instrument translation module, the medical integration system 102 enables the generation of multi-lingual studies.

In one exemplary embodiment, the questions included in an instrument are associated with alerting features. The medical integration system 102 generates alerts by enabling physicians to establish answer threshold values for a question or an instrument. In this embodiment, if a patient fills out an instrument and the patient's answer to a particular question or questions exceeds a threshold value, the medical integration system 102 generates and sends the physician a notification message (e.g., an email or an alert icon is posted on a physician dashboard graphical user interface). In a particular example, for the question "on a scale of 1-10 how much pain do you experience in your knee when you wake up in the morning?," a physician establishes an answer threshold value of 8, indicating that system 102 generates and sends a notification message to the physician when a patient selects a value of 8, 9 or 10 in answering this question. The notification messages may be posted on a dashboard graphical user interface generated by the medical integration system 102, providing physicians with a quick view of responses to a physician's instrument without the physician having to review many instruments to ascertain where patient responses exceed predefined answer threshold values.

In another exemplary embodiment, instruments may be assigned a predetermined availability date: the date on which the instrument becomes available to the user. In one particular example, this date is set directly through a value being entered into a textbox by a user. In another particular example, the date is indirectly set by a reference to a number of days, weeks, months or years (e.g., 10 weeks from today). Instruments may also be assigned a duration of availability. During this duration (e.g., a number of days, weeks, months or years), the instrument is available for a user to complete.

Instrument Validation Module

In the exemplary embodiment described herein, when a customized instrument is generated, a new set of questions included in the customized instrument are reviewed, rated and validated in many review phases, with an individual phase modifying and/or eliminating questions until the instrument is final. Frequently, associations, institutions and clinics assemble expert panels to validate the custom generated instruments prior to the instruments' deployment to patients. In this case, the medical integration system 102 may generate online review forums to serve a global set of researchers or a single organization/clinic or physicians, reviewers and experts (collectively referred to as "panel members" herein, without limitation, for purposes of convenience). The review forums allow a physician or researcher who generated the study (collectively referred to as "submitter" herein, without limitation, for purposes of convenience) to submit the questions to be refined to the panel members in a secure, distributed and online environment. Through the review forums, for example, questions are viewed, commented on, rated and verified collaboratively by the panel members.

FIG. 11A illustrates a particular exemplary embodiment described herein. Referring to FIG. 11A, the medical integration system 102 generates a graphical user interface 300 that includes, for example, a visual representation of a virtual forum for the panel members to collaborate and review an instrument. In this illustrated example, section 302 of the graphical user interface 300 includes a list of postings 304, 306, 308, 310 made by the various panel members for an instrument. The illustrated postings 304, 306, 308, 310 include threaded discussions linked to a particular question or feature of the instrument (e.g., the instrument timeline). Panel members collaborate with one another for private discussions using threaded discussion boards before passing information onto the submitters of the instrument. As the submitters respond to the postings 304, 306, 308, 310, the submitters' responses are added to the threaded discussion.

In one exemplary embodiment, the review forums include a rating system, through which panel members access tools to rate an instrument, including a list of predefined questions to consider in reviewing the instrument. The rating system enables the panel members to rank the quality of a question and the question's associated score system and numerical score.

In another exemplary embodiment, the review forums also include a scoring validation system to validate the scoring system associated with an instrument. Through the scoring validation system, panel members may review and comment on the validity of the scoring system associated with the instrument and the validity of the numerical scores assigned to individual questions within an instrument.

When a submitter and panel members have completed review of an instrument (e.g., single or multi-centered studies), the medical integration system 102 permits the electronic generation of trial studies to further validate the instrument and its questions and score system. During trial studies, for example, the medical integration system 102 engages patients to participate in the trial study, by emailing the finalized instrument to patients and soliciting feedback (e.g., feedback regarding study length or understandability of a question). Patients may provide feedback through the review forums, which include a section for a clinical trial threaded discussion.

In the exemplary embodiment described herein, through the medical integration system 102, a finalized instrument (i.e., a finalized customized and non-customized instrument) may be sent to patients to participate in the study. Patients are selected to participate in a study by the patient's physician, based on the patient's qualifications, including, for example, age and gender. Physicians are able to enter patient name and other identifying information (e.g., email address and home address) into the medical integration system 102. In this embodiment, the medical integration system 102 also queries data repositories, including EMR systems, for the names of patients qualified to participate in a study. The medical integration system 102 may generate a list of the patients qualified to participate in a study and may enable a user to link (e.g., through a pointer) a selected patient to a particular study. As a result of the link, the system 102 may generate a notification message notifying the patient that he has been selected to participate in a study. In some examples, the patient is notified by an electronic message sent to the patient's electronic mail address. In other examples where the patient has a user account with the medical integration system 102, the patient is notified through a dashboard message or alert displayed in the patient's dashboard graphical user interface when the patient logs into the medical integration system 102.

Referring to the illustrated example of FIG. 10, the medical integration system 102 may generate a dynamic instrument form graphical user interface 270 through which users view and complete an instrument. The illustrated dynamic instrument form graphical user interface 270 may include a form progress indicator 282, which displays a portion of the instrument completed by the user. In this illustrated example, the form progress indicator 282 also displays a visual representation of a percentage of questions completed.

The illustrated dynamic instrument form graphical user interface 270 also includes, for example, an auto-scroll feature (not shown), which allows users to easily navigate an instrument without the use of a scrollbar or a mouse wheel. Upon completion of a question within an instrument, the page automatically scrolls to the next unanswered question.

The dynamic instrument form graphical user interface 270 includes, for example, a read-only mode for the review of past instrument results. The dynamic instrument form graphical user interface 270 also includes a try-it mode which allows a user to view, fill out and score an instrument without any data being recorded in the database 126. Try-it mode allows physicians who are unfamiliar with an instrument to fully understand the instrument before assigning the instrument to patients.

In one exemplary embodiment, a skipped question manager may monitor skipped questions within an instrument. When a user skips a question, the manager marks and notifies the user (e.g., by a prompt box) before final submission of the instrument to the system 102. In another exemplary embodiment, an audio reader feature within the medical integration system 102 returns and plays an audio rendition of a current question as an instrument is being completed. This feature can be toggled on or off by the user. The audio files may be recorded and stored on the medical integration system 102 in a digital format and relate to the respective question. Multi-language support is provided for the audio recordings.

Frequently, multiple instruments may include questions that contain similar content and/or the same content. In this case, a condense similar question module condenses into a single view or graphical user interface questions across a single instrument or across multiple instruments that are similar in type and responses. The condensed view is then presented to the user. Through condensed views, the page size of an instrument may be reduced, generating the appearance of a smaller instrument that is more manageable for a user to answer. In a preferred embodiment, the condense similar question module executes rules that match pre-defined key words to words included in a question by comparing one or more characters included in the question to the pre-defined keywords. If multiple questions include characters matching (e.g., exact match, similar match or some variation thereof) the predefined keywords included the rule, the module generates a condensed view of the multiple questions including the matching characters.

Figure 11B:
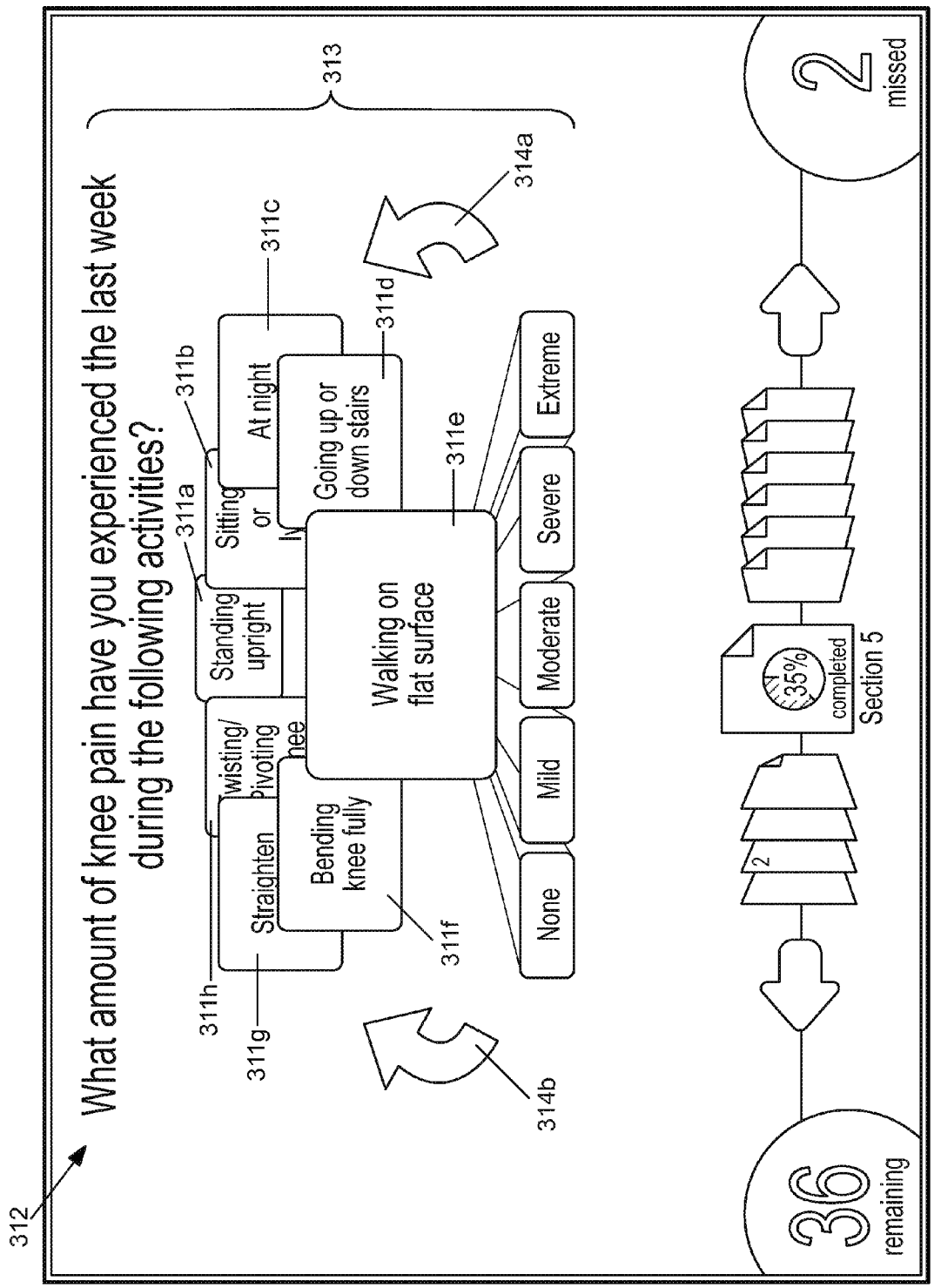

FIG. 11B illustrates a particular exemplary embodiment described herein. Referring to FIG. 11B, the system 102 generates a graphical user interface 312 that when rendered on a display device renders visual representations of eight questions 311a-311h as a condensed question 313 in a "carousel" form. The graphical user interface 312 includes, for example, links 314a, 314b. In this illustrated example, when a user selects a link 314a, 314b, the system 102 generates another graphical user interface which displays the next question causing the view of the questions 311a-311h to "rotate" the next question.

In one exemplary embodiment, the condense similar question module may generate follow up or adaptive questions, which are presented after a user has responded to a question. These adaptive questions ensure that the response a patient provides for a question corresponds to the various questions across multiple instruments. Through the condense similar question module, for example, a user provides answers for questions across various instruments. Through these provided answers, the system 102 generates scores for questions across the various instruments, based on the questions' specified scoring system and the user's provided answers.

In another exemplary embodiment, a reward point module allows users to earn points for the completion of an instrument. As a user completes an instrument, a predetermined number of points are issued and associated with the user's account. At the end of a study, the accumulated number of points may be applied towards the purchase of items. In a particular example, as a physician generates a study instrument, the physician may assign a reward package to the study. A reward package maps a number of points to one or more questions included in the instrument.

Control Panel

In the exemplary embodiment described herein, users may access the medical integration system 102 through a control panel. Once a user has logged into the medical integration system 102 through the control panel, users are presented with information to conduct studies, organize patients and manage data.

Figure 12:
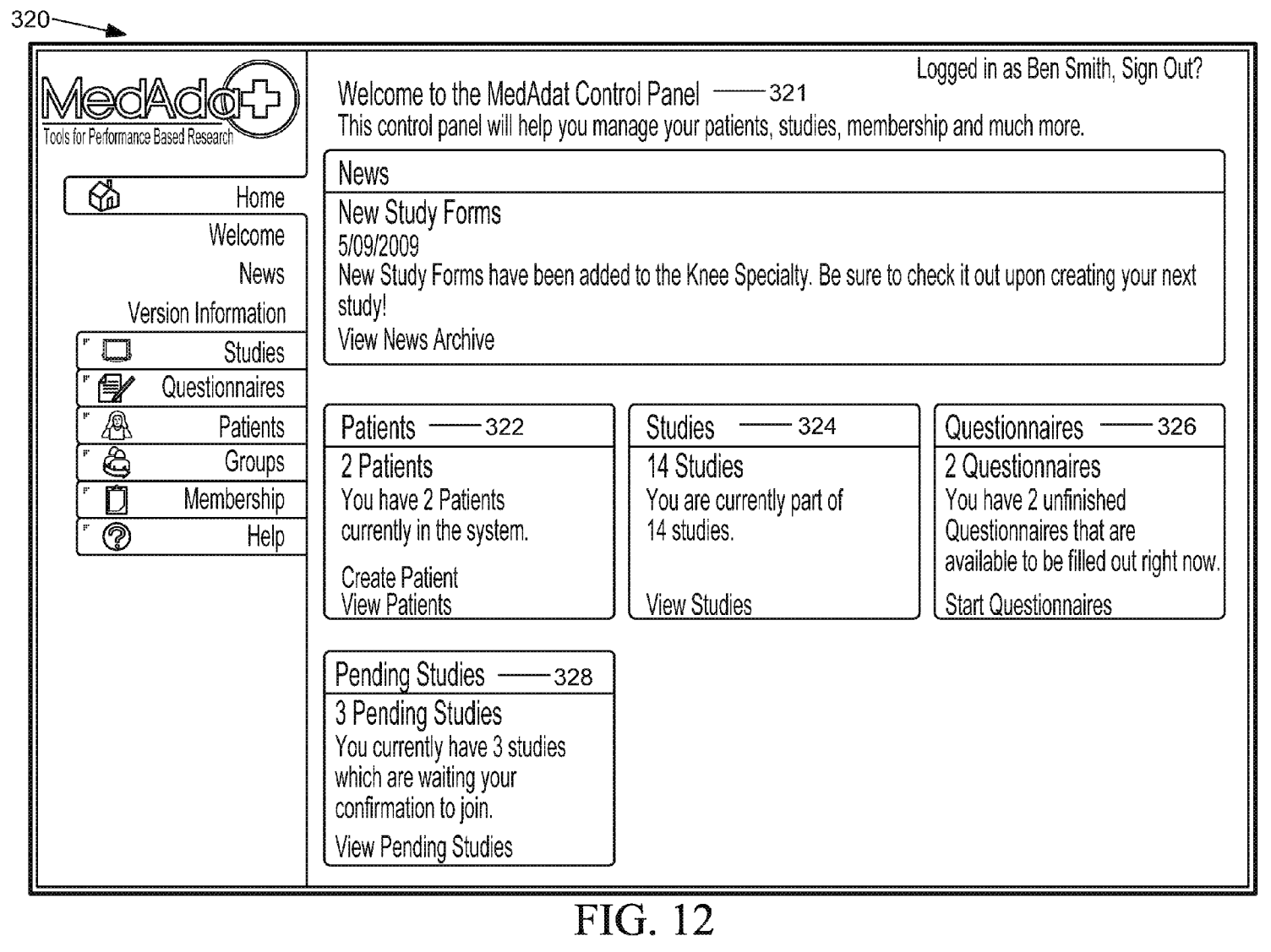

FIG. 12 illustrates a particular exemplary embodiment described herein. Referring to FIG. 12, the medical integration system 102 generates a graphical user interface 320 including, for example, a control panel 321 or a dashboard graphical user interface. In the illustrated example, a section 322 of the control panel 321 notifies a user of a number of patients enrolled in the medical integration system 102. Another section 324 of the control panel 321 notifies a user of the number of studies in which the user is a participant. In this illustrated example, another section 326 of the control panel 321 notifies the user of the number of unfinished instruments the user needs to complete. Another section 328 of the control panel 321 notifies the user of a number of pending studies the user needs to join.

In one exemplary embodiment, an account information section of the control panel allows users to view and edit user account information, including the following information: first and last name information, gender information, race information, primary language information, date of birth information, and contact information (i.e., street address, city, state, zip code, email address, telephone number, mobile number and fax number). In another exemplary embodiment, through the control panel, a user changes the user's account password by inputting the original password, a new password and confirming the new password. Through the control panel, the user may specify the frequency (e.g., once, once a day or once every twelve hours) for which notification messages (e.g., emails) regarding the tardiness of an instrument's completion are sent.

Another section of the control panels allows, for example, a user to view the available instruments included in the database. Through a selectable link, a user may choose to view instruments, including specialty instruments (e.g., forms that are specific to knee issues) and custom instruments (e.g., instruments that have been customized for a clinic or instruments that are custom generated).

The control panel may also enable a user to manage studies by viewing information about studies, participating in studies and viewing study invitations, for example. The control panel may provide a search box through which users of the medical integration system 102 search for various studies and instruments.

Figure 13:

FIG. 13 illustrates a particular exemplary embodiment described herein. Referring to FIG. 13, the medical integration system 102 generates a graphical user interface 340 including a manage studies section 341 of the control panel. In this illustrated example, the user is provided with a list of the studies generated by the user and the studies in which the user is a participant. The list includes, for example, the study name 344, a link 346, selection of which displays various details associated with the study, the number of patients in the study compared to a goal number of patients needed in the study 348, compliance information 350 (e.g., a percentage of instruments that have been completed), a study start date 352, a study end date 354, IRB status information (e.g., a stage of the IRB approval status), whether the study has been sent to the IRB, whether the study is pending IRB approval and communication, whether the IRB has approved the study, and whether the study is available to patients. The pending instruments portion of the control panel includes, for example, a listing all the pending instruments the user must complete.

The control panel may also provide the user with a list of pending instruments, including for example the following information: the name of the instrument, the patient to which the instrument has been assigned, the date the instrument became available, the date the instrument access expires, a numerical representation of the number of days left before the instrument access expires, a current status of the instrument (e.g., the instrument has not been started, the instrument has been started but not completed), a list of the questions in the instrument that have been completed and have a selected response, and a link to the instrument to begin completion.

In the exemplary embodiment described herein, the control panel may provide the user with a "study invitations" list: a list of the studies that the user has been invited as a participant. The study invitations list includes, for example, the study name and a link to view various details associated with the study, the name of the physician who generated the study, a brief description of the study, and a link 356 through which the user accepts or declines the invitation to participate in the study. The control panel may also include a section for users to assign instruments to patients and doctors. By assigning an instrument to a patient or a doctor, the patient or doctor is notified of the assigned instrument and of the need to complete the instrument.

In one exemplary embodiment, an instrument history section of the control panel displays a visual representation of the instruments completed by a patient and various completed instrument information, including, for example, the name of the instrument, the name of the patient who completed the instrument, the name of the physician who assigned the instrument, the date the instrument closed accessibility, the current status of the instrument, and a view of the individual responses of the instrument.

In another exemplary embodiment, the control panel may also include an instrument profile section which displays a visual representation of a pre-defined collection of instruments that are grouped together as a profile. These collections of instruments are used for ease of assigning commonly occurring instruments to patients. In one particular example, a collection of instruments, such as the SF-12 instrument, the KOOS instrument and the Marx instrument, used for new patients are collected into a profile called "New Patient."

The control panel may also include a manage patients section for adding/editing/deleting a patient-physician relationship. The manage patients section includes, for example, a search box through which the user searches for patients based on first or last name, the clinic with which the patient is associated, and the gender of the patient. Once the system 102 locates a patient, a user may edit the information associated with the patient and/or delete the patient information and instrument history associated with the patient.

In the exemplary embodiment described herein, an overdue instruments section of the control panel displays a list of the patients that have at least one overdue instrument (e.g., an instrument that has a status of "not started" or "not completed") and associated information, including for example the last name of the patient, the first name of the patient, the name of the clinic with which the patient is associated, an overdue count (i.e., the number of instruments that are deemed overdue), and a link to view the individual instruments that are overdue. Through selection of the link associated with an overdue instrument, the user has the option of extending the duration of time in which a patient has to complete the instrument or deleting the instrument from the list of instruments assigned to the patient.

The similar questions section of the control panel displays, for example, similar questions from other instruments based on a predetermined selected question included in a particular instrument as follows. The control panel displays a list of instruments available for use in a study. Based on the user's selection of a particular instrument, the medical integration system 102 may display the questions included in the selected instrument. Based on the user's selection of a particular question within the selected instrument, the medical integration system 102 may also determine other instruments with similar questions and display associated information, include for example: the name of the instrument including the similar questions, the question number within the respective instrument, the text of the actual question within the respective instrument, and whether the medical integration system 102 determined the similar question in the respective instrument to be an exact match or a similar match or some combination thereof.

In one exemplary embodiment, the print instrument section of the control panel allows users to select print parameters for the available instruments in the medical integration system 102. Before printing, the user may select whether the instrument is printed in color, black & white or grey scale. The user also selects the font size of the content within the instrument to suit the user's visual needs. Additionally, the printable instrument defaults to the print in the user's default language. Once the print parameters are selected, the user may download and print the instrument.

In another exemplary embodiment, a manage groups section of the control panel allows the user to manage the groups the user has invited to participate in a study, for example by editing (e.g., adding members to a group) and deleting groups. The manage groups sections may also include a groups list with the following fields: the group name, the description or purpose of the group, and the number of members in the group.

The control panel also includes, for example, a manage users section for adding and/or editing and/or deleting other users stored in the database 126 of the medical integration system 102. Users may locate other users by performing a first and/or last name user search and/or a clinic search (e.g., a search for the user based on the clinic with which the user is associated). The medical integration system 102 determines the names of users matching the entered search criteria and displays the search results based on first name, last name and/or clinic association information.

In the exemplary embodiment described herein, the control panel includes an IRB management section which allows users to manage IRB submissions by the physician generating the study. IRB management section eases the relationship and the transfer of documents between the IRB and the physician. An instrument submission from a physician is added to the IRB management section of the control panel, for example, along with study information, consent forms and other required documentation required for IRB approval.

Access to the Medical Integration System

Users access the medical integration system 102 in various ways, including, for example, portal access, clinic access and email link or uniform resource location ("URL") access. For portal access, users of the medical integration system 102 may be assigned account information (e.g., a username and a password) and may access the medical integration system 102 through a web page or other access graphical user interface using the assigned account information. To log into the user's account, the system 102 verifies the user's username and password combination. Once a valid combination has been given, the user may be prompted with a security question, which the user generated during account setup.

To keep up with the fast paced traffic that many clinics receive, the medical integration system 102 enables "clinic access," in which a clinic authorizes system access on a computer (e.g., a dedicated machine or kiosk), thereby enabling a simplified login process. Once a computer has been authorized and designated as a "clinic machine," the login process includes, for example, the user inputting the user's full name and date of birth information into the system 102 to access the user's account or a particular instrument or to access the user's appointment with a physician.

Some patients prefer not to access the medical integration system 102 through a username and password combination. To accommodate these patients, the medical integration system 102 enables email link and URL access by sending the user an electronic message (e.g., text message, email message or a SMS message) with an embedded link (e.g., URL hyperlink) through which the user accesses the system 102.

Clinics and other users (e.g., researchers and physicians) may also purchase a membership on a per clinic basis or on a per use basis to access the medical integration system 102. System membership allows a user to access the system 102 a specified number of times or an unlimited number of times.

In the exemplary embodiment described herein, users of the medical integration system 102 may be assigned a system role, which determines the permission level available to the user and the system functionality provided to the user. Some users are assigned multiple system roles and different system roles for different clinics. The types of system roles include, for example, clinic administrator, to manage the doctors and physician assistants associated with a clinic and to perform other administrative tasks, including managing patients' addresses, payments and other system membership information. Other system roles include, for example, the physician role, the physician assistant role, the patient role and the IRB administrator role.

In one exemplary embodiment, system roles are associated with a permission level, including permission to generate a new study, join a study, add patients to an existing study, invite doctors to join a study, view the details of a study, post a message to all members within a study, assign instruments to users, generate a new patient profile for a clinic, view patients associated with a clinic, view clinic patients first names and last names, join a group, generate a group, search for groups, post messages to members in a group, edit the details of a membership, view memberships associated with a clinic, edit clinic memberships, associate physicians, physician assistants, and clinic administrators with a clinic, de-associate a user with a clinic and view overdue instruments.

In another exemplary embodiment, user actions performed within the medical integration system 102 are logged. Various user actions performed within the medical integration system 102 may be executed by the system 102 through backend database queries. These queries may be logged and saved, providing a record of a user's identity and a time when information was accessed and providing a record of the type and the content of the accessed information.

Global Research Database

In the illustrated example of FIG. 1, as patients complete instruments, the medical integration system 102 receives instrument data (e.g., answers to the questions included in the instruments) and stores this received instrument data in one or more databases 126. In this example, patients access and complete instruments by accessing the instruments over the illustrated network 112 (e.g., the Internet or an intranet). Accordingly, the instrument data may be sent over the network 112 to the medical integration system 102 and may be stored in the database 126. Database 126 may include multiple databases running on the same machine or on different machines.

In the exemplary embodiment described herein, database 126 stores de-identified instrument data to protect patients' privacy and offer a research space for researchers worldwide. The instrument data may be de-identified by removing patient name, address, and other demographic data to comply with the Health Insurance Portability and Accountability Act ("HIPAA") and other privacy concerns. In doing so, the physician losses access to data associated with the physician's patients, instruments and submissions. To enable a physician who generated the instrument to locate the physician's patients and access fields (e.g., name and address information) that the physician is entitled to access, the de-identified data may be linked or otherwise associated with an identifier, including without limitation a unique identifier, a numerical identifier and an encrypted identifier (e.g., an encrypted hidden code) (collectively referred to as an "encrypted identifier" herein, without limitation, for purposes of convenience.) Through the encrypted identifier, the physician may access, view and identify information removed during the de-identification process and associated with the physician's patients. In one particular example, the encrypted identifier may be generated by the system 102 using a random number generator as is commonly known in the art.

In this exemplary embodiment, the encrypted identifier enables physicians to collaborate with each other and to plot de-identified patients' data in comparison to other patients' data stored in the database 126, including a physician's patients—which are identifiable through the encrypted identifier. In one particular example, a physician may plot how the physician's patients compare to patients in another world/country/state/region/city.

In one exemplary embodiment, the database 126 may be structured to enable collaborators to generate a private research space within the medical integration system 102. Collaborators share data within the private research space and with others if they choose to do so. Additionally, the database 126 may include a public space. The public space includes, for example, the information and data which is accessible to all users and members of the medical integration system 102.

The medical integration system 102 also includes, for example, an integration module, which is compliant with HIPAA and which allows the various processes, modules and sub-systems associated with the medical integration system 102 to communicate with one another and access the data stored in the database 126.

Data Mining and Research Tools Module

In the illustrated example of FIG. 1, the medical integration system 102 also includes a data mining and research tool module 120 (collectively referred to as "research tool" herein, without limitation, for purposes of convenience), which may be an interactive component integrated with the database 126 and may be used to retrieve data (e.g., information regarding a particular study or instrument) stored in the database 126 based on selected criteria. Through the research tool, a user compares instrument scores, views instrument scores, and views individual patient scores for a particular instrument for various timeline points in a study.

The research tool includes, for example, a visual dynamic query tool to mine, retrieve and graph data from the various studies. The visual dynamic query tool includes a graphical user interface through which users of the medical integration system 102 generate queries and send the generated queries to the database 126. The research tool may also include a visual search tool though which a user of medical integration system 102 enters search criteria (e.g., an age range for patients, gender information, race information or a study name). In this particular example, based on the entered search criteria, the medical integration system 102 may generate a search query and queries the database 126 using the generated search query. The database 126 returns to the system 102 data matching the criteria included in the search query. The returned data may be formatted to fit a desired visual charting type. Additionally, the research tool 120 may execute statistical analysis rules to determine various statistical calculations, including, without limitation, average, mean, median and standard deviation calculations, for study scores, instrument scores and scores linked to a patient. In this example, the statistical calculations include statistical data points, which may include average or median calculations for a particular instrument within a study or for a particular subset of patients within a study.

Figure 14:
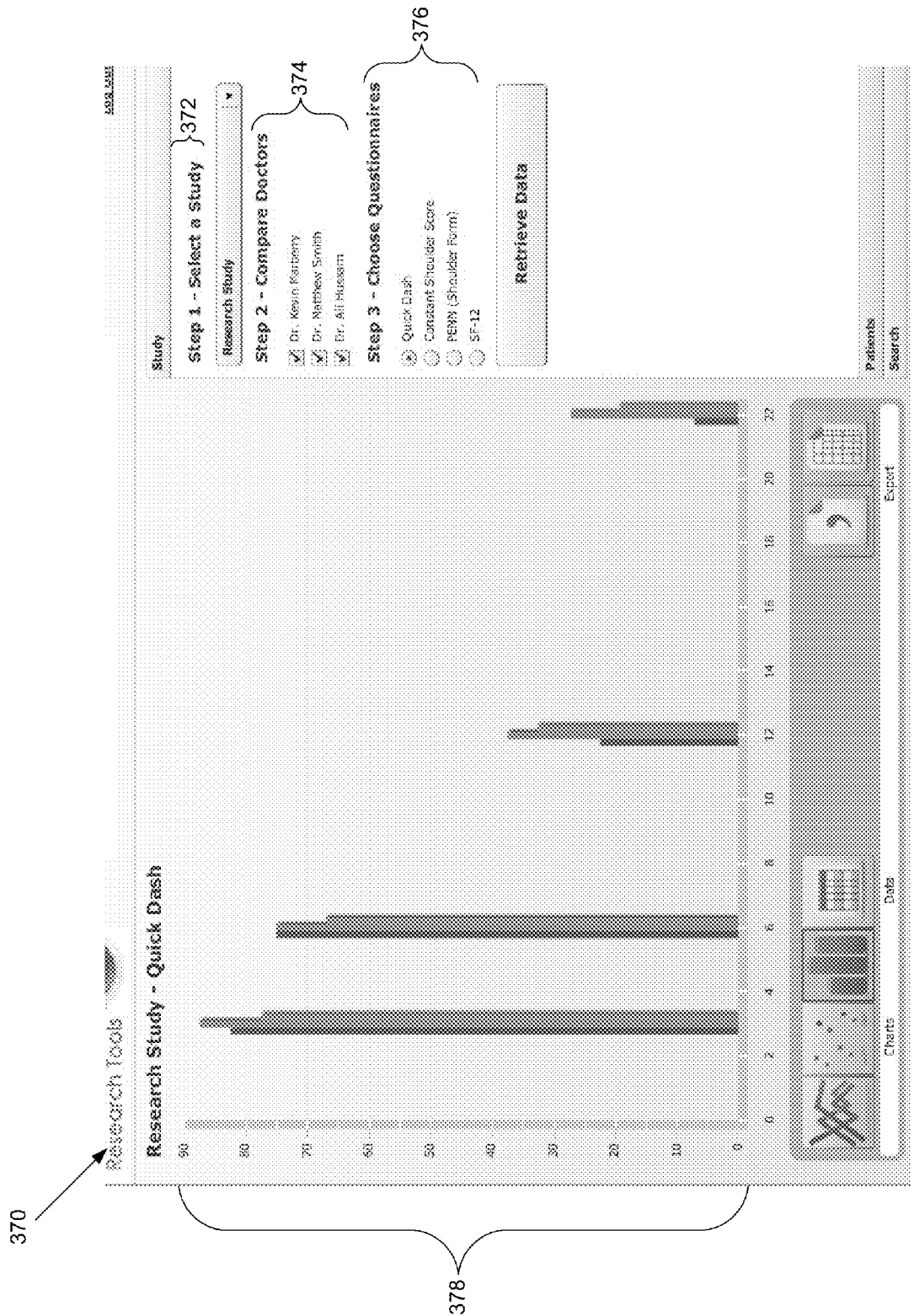

FIG. 14 illustrates a particular exemplary embodiment described herein. Referring to FIG. 14, the medical integration system 102 generates a graphical user interface 370 that displays a real-time chart representative of the executed queries and the data retrieved through the executed queries. The illustrated graphical user interface 370 includes a section 372 in which the user selects the study for which a real-time chart is generated. The illustrated graphical user interface 370 also includes a section 374 in which the user selects the physicians for which the user desires to view associated patient results. The illustrated graphical user interface 370 includes a section 376 in which the user may select the instruments within a selected study for which real-time data is charted. Based on the user's selected criteria, the illustrated graphical user interface 370 displays a chart 378 of the instrument scores associated with the selected instruments for the selected physicians.

In one exemplary embodiment, the medical integration system 102 includes an export data module to export and/or display data queried from the database 126 in a pre-defined format (e.g., a format that publications support and a format that conforms to medical journal and associations guidelines). In another exemplary embodiment, the medical integration system 102 also includes a multi-language module, which enables different language speaking researchers to communicate with each other in the researchers' native language. Through the execution of language rules which translate characters in a first language into a second language, the medical integration system 102 captures, executes, interprets and displays the review forums, instruments and queried data in the native language format of the researcher. Through the multi-language module, for example, the queried data is capable of being displayed in another, different language.

In one particular example, a German researcher queries the medical integration system 102 in German and sends the queried data to an American collaborator. The medical integration system 102 recognizes the language difference between the sender (i.e., the German researcher) and the recipient (i.e., the American collaborator) and displays and sends the query results in English to the American collaborator. Additionally, through the multi-language module, patients may complete instruments and data is input and saved into the databases 126 in one language. Through the multi-language module, the completed instrument data may be viewed and/or queried by a user of the medical integration system 102 using a second language.

Procedure Determination Module

The instruments described herein are often generated to test the efficacy of a procedure (e.g., a surgical procedure or a pharmaceutical treatment). In this case, through the use of the timelines described above, the system 102 may collect instrument data (through the various questions and answers) pertaining to a patient's symptoms, pain level, disability level or any other patient attributes (collectively referred to as "disability level" herein, without limitation, for purposes of convenience) before the procedure ("before procedure questions") and after the procedure ("after procedure questions"). In a preferred embodiment, a physician links a procedure identifier (e.g., a procedure code or a procedure description) to the instrument. As the database 126 collects and stores the patient's answers to the questions included in the instrument, the answers are associated with the procedure identifier. In this preferred embodiment, the database stores a list of symptoms associated with a procedure, where the symptoms are categorized as those symptoms occurring before the procedure and those symptoms occurring after the procedure.

In the exemplary embodiment described herein, the medical integration system 102 may also include procedure assessment rules, which "grade" or classify a procedure based on the determined efficacy of the procedure. In a particular example, the procedure assessment rules collate the patient's symptoms before the procedure and the patient's symptoms after the procedure to determine if the patient's symptoms have improved following the procedure. For the procedures which improve a patient's symptoms, the procedure assessment rules may categorize those procedures as being effective.

The medical integration system 102 also includes, for example, procedure determination rules to determine a recommended procedure or a recommended medical device based on patient's symptoms and an instrument's score values, including, for example, symptom severity score values and symptom improvement score values. The medical integration system 102 generates the procedure determination rules by determining the medical procedures that have been categorized as effective ("effective medical procedures") based on the score values associated with a user's answers to various questions in an instrument. In one particular example, the system 102 determines the efficacy of a joint replacement surgical procedure. A before procedure question includes the following question: "What level of pain are you experiencing in your joint?" The symptom improvement score values associated with this question include, for example, "1", "2" and "3". A score value of "1" is indicative of a high pain level. A score value of "2" is indicative of a moderate pain level. A score value of "3" is indicative of a low pain level. In this example, the after procedure question includes the same question (i.e., "what level of pain are you experiencing in your joint?") as the before procedure question with the same associated score values. If a patient answered the before procedure question with a "high pain level" answer (i.e., a symptom improvement score value of "1") and the after procedure question with the "low pain level" answer (i.e., a symptom improvement score value of "3"), the system 102 categorizes the joint replacement surgical procedure as an effective medical procedure, based on the symptom improvement score value increasing from a value of "1" to a value of "3."

In the exemplary embodiment described herein, for the effective medical procedures, the medical integration system 102 generates a procedure determination rule including the symptoms patients experienced before the procedure. In a particular example, a procedure determination rule for joint replacement includes the following instructions "If symptoms=joint pain or joint difficulty or joint swelling, then procedure=joint replacement." When a user inputs a patient's symptoms into the system 102, the procedure determination module 122 in this example executes the procedure determination rules by matching one or more characters included in the input symptoms to the symptoms included in the procedure determination rules. Based on returned symptom matches, the procedure determination rules generate a list of recommended procedures.

Patient Flow Module

Busy clinics experience patient overload that results in patients waiting longer to see a physician. As wait times increase, patient satisfaction with a patient's physician and/or clinic experience decreases. In the illustrated example of FIG. 1, the patient flow module 124 improves patient satisfaction by efficiently tracking actions a patient needs to take and instruments a patient needs to fill out prior to engaging with a physician. The illustrated patient flow module 124 is integrated with various aspects of the medical integration system 102, including, for example, the database 126. Through querying the database 126, the patient flow module 124 determines the instruments a patient needs to complete prior to a consultation with a physician. The patient flow module 124 may also track a patient's steps and activities from the time the patient arrives at the clinic, registers with the clinic, waits to see a nurse, is seen by a nurse and is moved to an examination room. In a preferred embodiment, the module 124 provides clinics (e.g., physicians and nurses and health care providers) feedback and guidance as to the next action to be performed and the information the patient needs to provide the clinic, physician or nurse. By tracking this information, the patient flow module 126 facilitates moving patients through the clinic check-in process more quickly and thereby alleviates patient wait time. The module 124 may also manage patient load by alerting health care providers of the steps that need to be taken to move patients through an examination.

To facilitate quick and easy check-in once a patient has arrived at a clinic, the medical integration system 102 may generate a portal environment through which a patient accesses the medical integration system 102 to view the patient's appointment by entering patient information, including, for example, name information, date of birth information and/or selecting the name of the patient's doctor at the clinic. In a preferred embodiment, using the entered information, the medical integration system 102 queries the database 126 for the patient's appointment and determines the physician with which the patient is scheduled for an appointment. The module 126 may also query the database 126 to determine a listing of one or more instruments which the patient's physician requires the patient to complete prior to the consultation.

Figure 15:
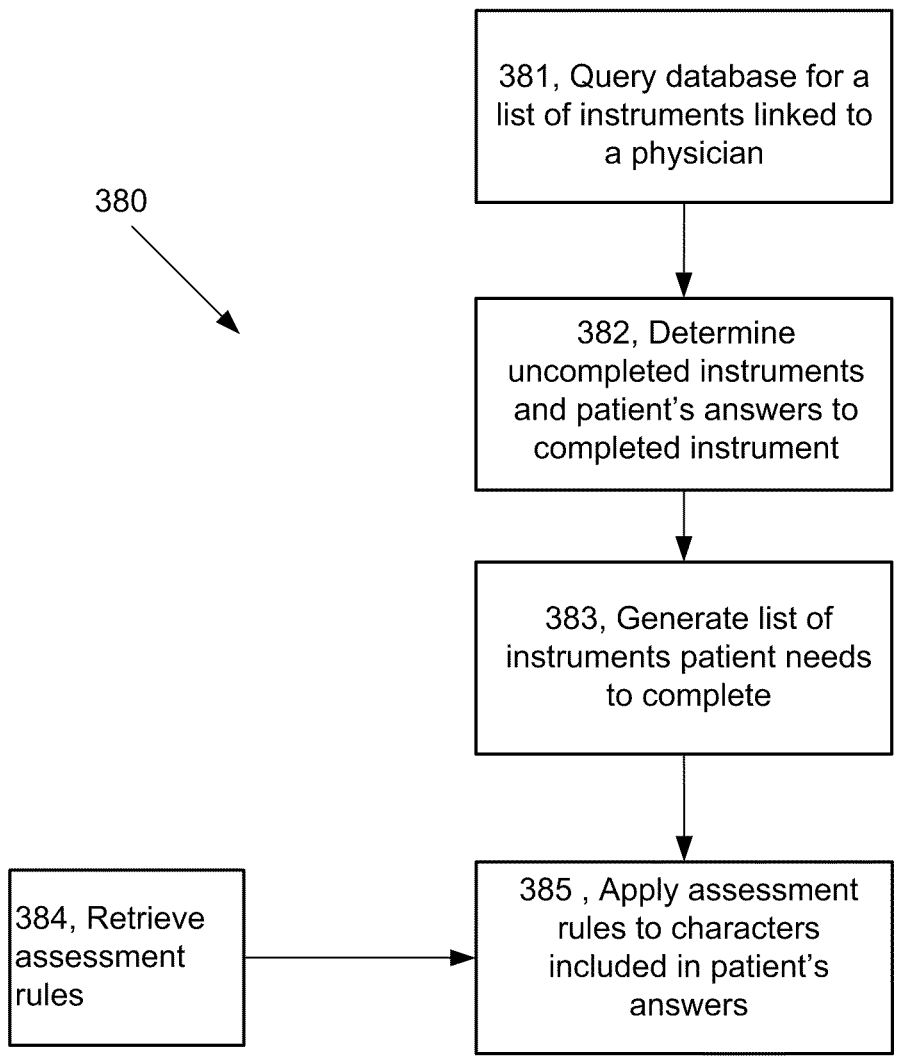

FIG. 15 illustrates a particular exemplary embodiment described herein. Referring to FIG. 15, the patient flow module 124 performs 380 various actions in tracking a user's appointment with a physician. The patient flow module 124 queries 381 the database 126 for a list of instruments linked to a physician thereby determining the instruments a physician requires a patient to complete prior to an examination. In this illustrated example, based on the query results, the patient flow module 124 determines 382 a list of instruments the patient needs to complete and the content of answers for the questions in a completed instrument. Additionally, in this illustrated example, the patient flow module 124 generates 383 a list of instruments the patient needs to completes and generates a graphical user interface that includes this list, as described in further detail below.

In the exemplary embodiment described herein, the database 126 may store medical assessment rules (i.e., instructions for how the system 102, the patient flow module 124 or a process executed by the system 102 analyzes and assesses the content of a user's answers to questions included in an instrument.) Through execution of the medical assessment rules, the system 102 determines, without limitation, diagnosis information, treatment information and medication information for a patient. The system 102 generates the medical assessment rules by receiving a listing of symptoms (e.g., symptoms regarding pain) and a listing of medical diagnoses associated with the symptoms. In a particular example of a medical assessment rule, if the system receives patient symptoms indicating that the patient is experiencing pain when opening a jar, then the patient is assigned an assessment of "wrist pain."

In the illustrated example of FIG. 15, the patient flow module 124 retrieves 138 the medical assessment rules from the database 126 and applies 385 the assessments rules to the content and characters included in the patient's answers. Through the application of the medical assessment rules, the patient flow module 124 may generate a list of diagnoses and treatments applicable to the patient.

Figure 16:
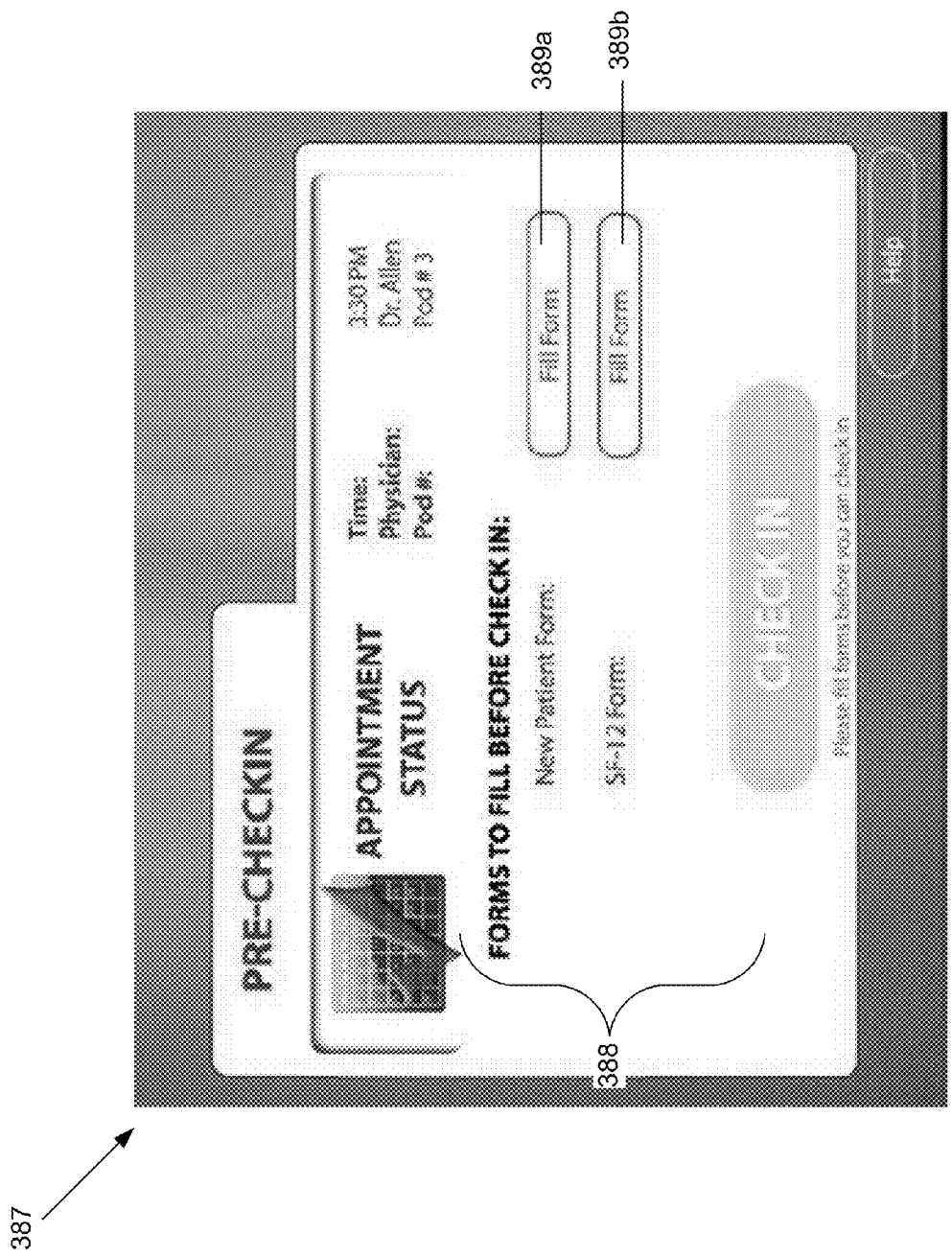

FIG. 16 illustrates a particular exemplary embodiment described herein. Referring to FIG. 16, the medical integration system 102 generates a graphical user interface 387 that when rendered on a display device displays a visual representation 388 of the names of the forms that need to be filled out by the patient. The illustrated graphical user interface 387 also includes links 389*a*, 389*b*, selection of which cause the medical integration system 102 to generate another graphical user interface that displays the contents of the instrument associated with the selected link. In a preferred embodiment, as a patient fills out and completes the selected instruments, the patient's entered data and answers are saved in the database 126, allowing the patient's entered data and answers to be viewed both by the patient's physician and by other researchers and collaborators querying the database 126, as described above.

Referring to the illustrated example of FIG. 1, the patient flow module 124 also notifies health care providers, including physicians and nurses, of the instruments a patient has already completed. In a preferred embodiment, the illustrated patient flow module 124 generates an electronic message including a list of the names of the completed instruments and the system 102 sends the electronic message to the health care provider. Additionally, the module 124 enables the health care providers to add additional instruments to the list of instruments for a patient to complete. Referring to the illustrated example of FIG. 16, these newly added instruments may be displayed in graphical user interface 387, notifying the patient of the newly added instruments.

Figure 17:
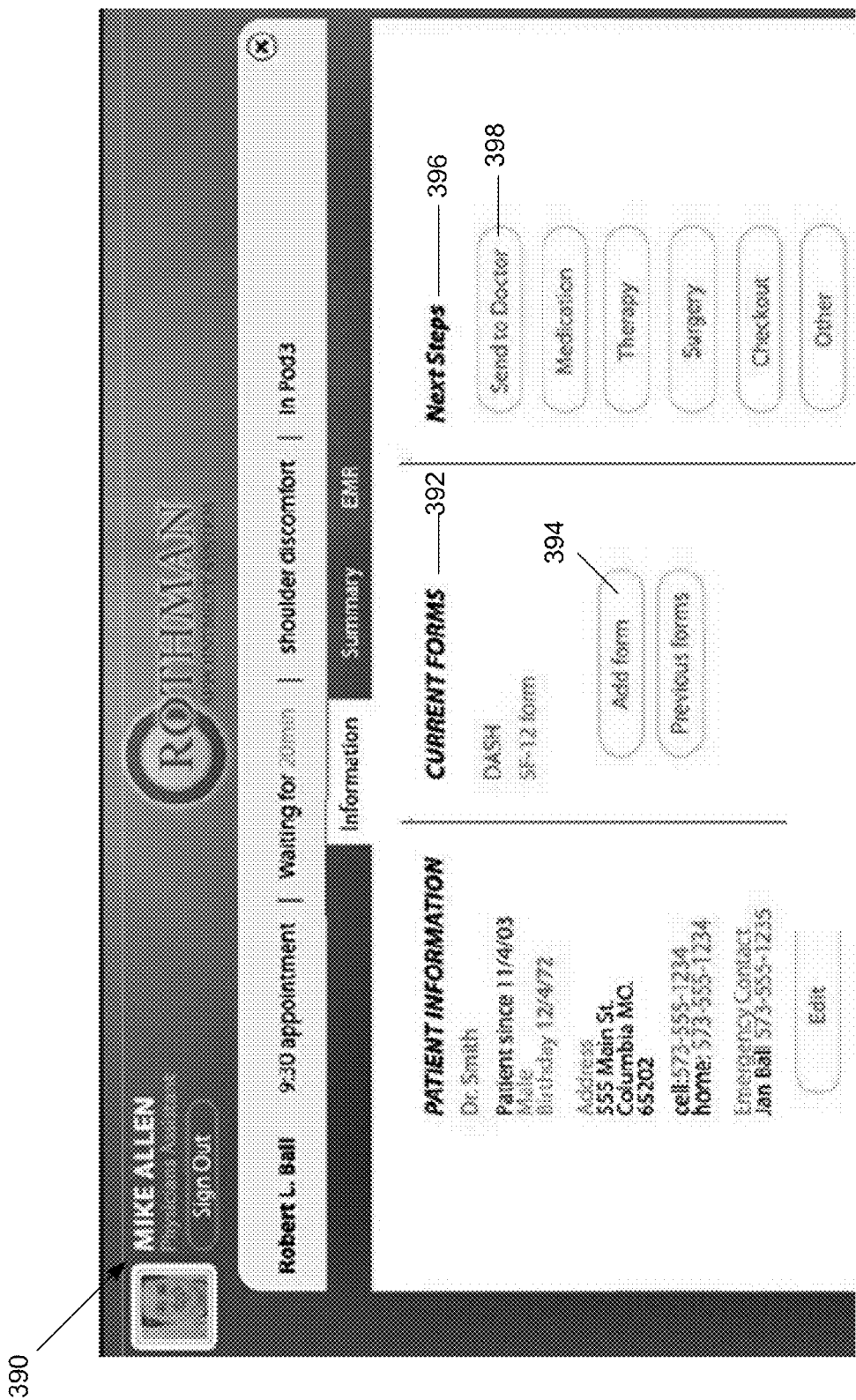

Referring back to the illustrated example of FIG. 1, the patient flow module 124 facilitates information flow and continuing of medical care by enabling health care providers to send completed instruments to other health care providers and external and internal EMR systems. FIG. 17 illustrates a particular exemplary embodiment described herein. Referring to FIG. 17, the medical integration system 102 generates a graphical user interface 390, with illustrated section 392 displaying a list of the instruments with which a patient is currently associated and which the patient needs to complete. Through selection of the illustrated link 394, a health care provider adds another instrument to the list of instruments the patient needs to complete. Section 396 of the illustrated graphical user interface 390 enables a user to send a completed instrument to a recipient (e.g., a physician), through selection of link 398, thereby facilitating continuity of medical care.

In the illustrated example of FIG. 1, the patient flow module 124 interacts with appointment systems and EMR systems 128 to enable health care providers to manage appointments, monitor patient flow in a clinic and perform the proper processes and tasks needed move patients through the clinic. In a particular example, the system 102 retrieves a physician's appointment schedule from the database 126 or another appointment schedule system. A physician's appointment schedule includes the names of the patients schedule for a visit with the physicians. In this example, if a physician is overbooked or double booked, the module 124 enables a user to associate one or more of the physician's appointments with another physician, thereby decreasing the amount by which one physician is overbooked and decreasing the amount of time a patient needs to wait to see a physician.

In the exemplary embodiment described herein, the patient flow module 124 may query the database 126 for a list of instruments completed by a particular patient. The module 124 may apply the medical assessment rules, described above, to analyze the patient data (e.g., answers to the questions included in the instrument) and to generate a visual representation of the health problems and issues experienced by the patient. In this embodiment, the visual representation enables health care providers to quickly and accurately assess a patient's condition, saving the health care provider time in diagnosing a patient's health problems.

Figure 18:
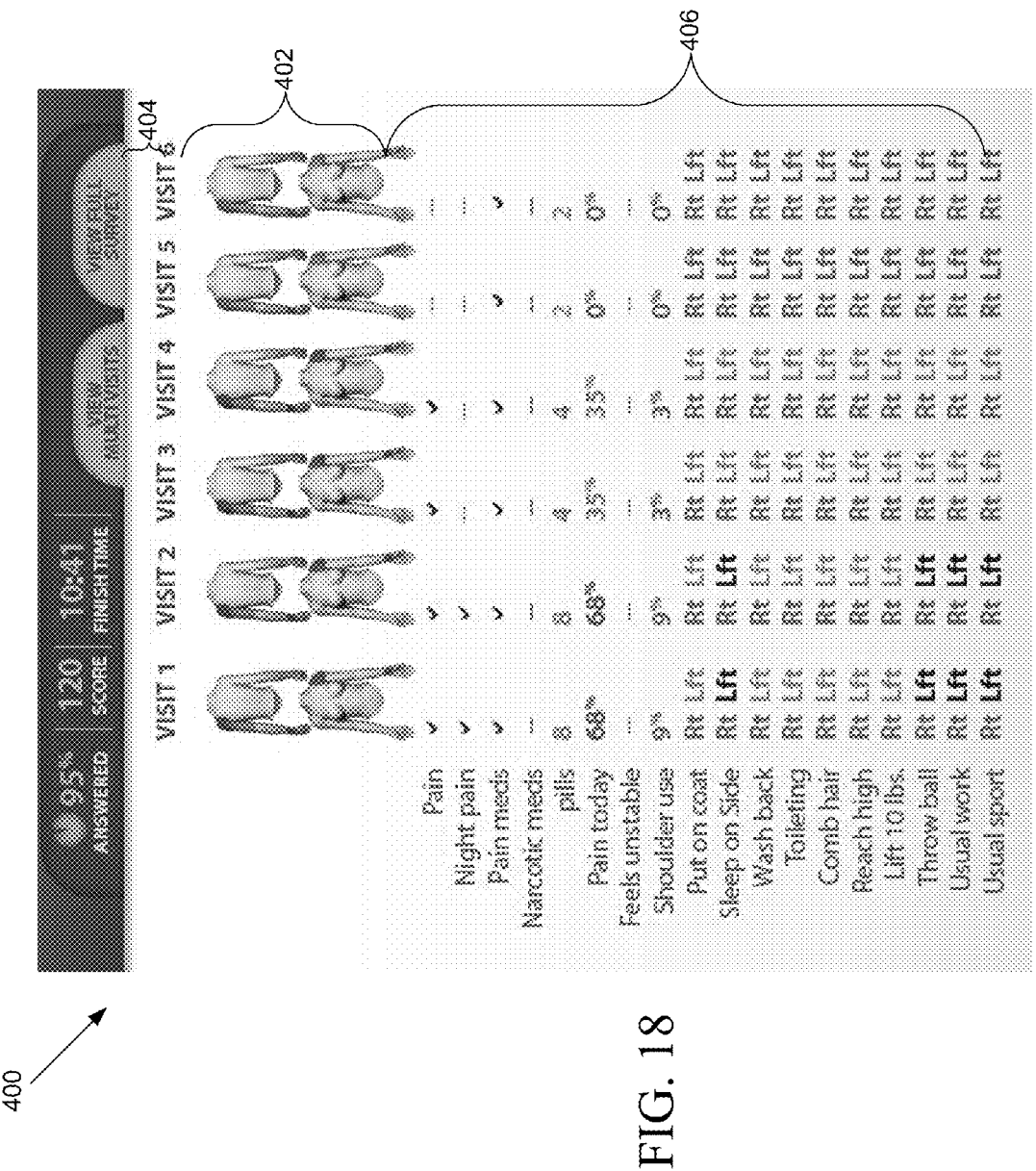

FIG. 18 illustrates a particular exemplary embodiment described herein. Referring to FIG. 18, the medical integration system 102 generates a graphical user interface 400 including one or more visual representations 402 of a section of the patient's anatomy in which the patient is experiencing pain or a medical issue. Section 404 of the illustrated graphical user interface 400 chronicles these visual representations 402 as a function of time or medical visits with the physician or clinic. Illustrated section 406 of the graphical user interface 400 includes, for example, metrics associated with a patient's treatment, diagnosis and symptoms. Illustrated section 406 is also represented as a function of time or visits in comparison to section 404.

Data Filter

Referring back to the illustrated example of FIG. 1, the medical integration system 102 may also include a data filter module 127. In the exemplary embodiment described herein, users of the medical integration system 102 upload medical data (e.g., research data, research records, surgical data, medical information data, electronic health records, paper health records, physician notes from prior and/or past visits to a medical facility, health information, medical status information, medical history information, and the like) into the system 102. For the system 102 to store, mine and access the uploaded data, the data filter module 127 may format the uploaded medical data such that the research tool 120 can mine the formatted data. The system 102 is able to access and mine data that comports with data format specifications corresponding to data fields in the instruments stored in the database 126. To format the data, the data filter module 127, for example, uses templates with fields that correspond to various fields associated with the instruments. As used herein, the terms "correspond" and "correspondence" (and all variations thereof) refer broadly to any sort of pre-defined or pre-existing relationship. Through the exemplary templates, the uploaded data is mapped into an acceptable format that can be read by the data filter module 127. The data filter module 127 formats the uploaded data such that data may be inserted into various fields associated with the instruments and read by the system 102.

In one exemplary embodiment, the instruments (e.g., pre-defined instruments and customized instruments) include fields, with each field specifying how data associated with that field is formatted such that the data is accessible by the system 102. The system 102 may perform various processes and may use templates in mapping the data uploaded to the system 102 to the fields in the instruments. As described in further detail below, through the templates, the uploaded medical data may be categorized to correspond to particular instruments (e.g., through the use of templates) such that the data may be formatted according to the formatting standards of the particular instrument and later inserted into the appropriate fields of the particular instrument.

Figure 19:
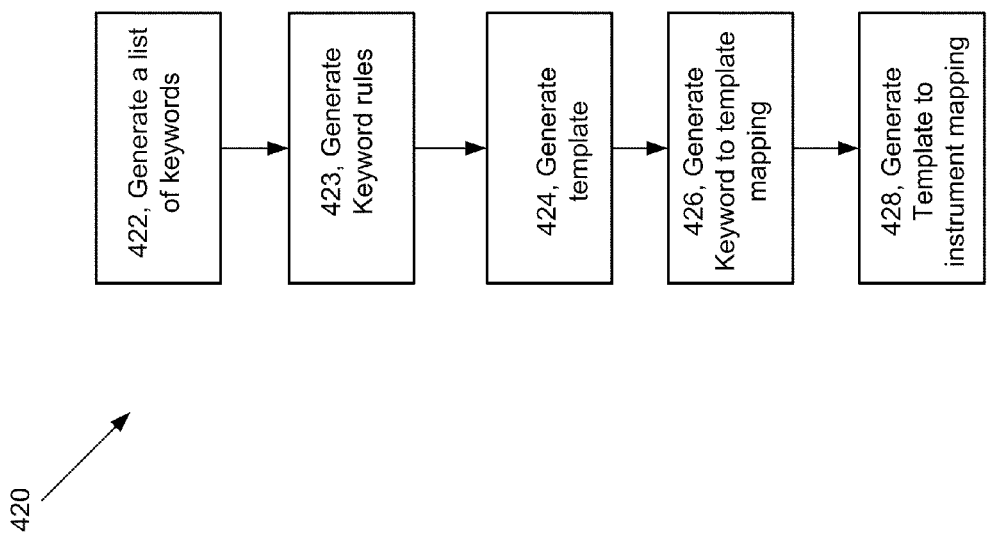

FIG. 19 illustrates a particular exemplary embodiment described herein. Referring to FIG. 19, the illustrated medical integration system 102 executes 420 and combines various processes including the following. In this exemplary embodiment, the medical integration system 102 generates a list of keywords that are, for example, associated with the various fields of the instruments. As used herein, the term "generate" is understood to refer broadly to any process and/or technique that produces and/or creates any data item, object and/or structure. In one exemplary embodiment, the system 102 includes a scanning tool (e.g., an optical character recognition ("OCR") scanning tool) that scans the text of the instruments stored in the database 126 and, based on the scanning, generates a list of keywords, for example, a list of the medical terms included in the questions included in the instruments. In another exemplary embodiment, the keywords include the questions included in the instruments. Based on the generated keywords, the system 102 stores the list of the generated keywords in the database 126.

In the exemplary embodiment described herein, the medical integration system 102 also generates 423 keyword rules associated with the keywords. The keyword rules may indicate the actions the system 102 should take when a keyword is detected in the medical data uploaded to the system 102. In this embodiment, the keyword rules specify that when a keyword is detected in the medical data uploaded to the system 102 that information included in the uploaded data and associated with the keyword (e.g., an answer to a question included in an instrument) should be selected by the system 102. In one particular embodiment, a keyword (referred to as "keyword A" herein, without limitation, for purposes of convenience) corresponds to a question (referred to as "question A" herein, without limitation, for purposes of convenience). A keyword rule (referred to as "keyword rule A" herein, without limitation, for purposes of convenience) specifies that the system 102 should select the answer (referred to as "answer A" herein, without limitation, for purposes of convenience) to question A, such that the text corresponding to answer A may be input into the appropriate template field, as described in further detail below.

In one embodiment, the system 102 also generates 424 a template that is associated with a particular instrument or with a series of instruments. The template includes fields (referred to as "template fields" herein, without limitation, for purposes of convenience) corresponding to fields in the instrument (referred to as "instrument fields" herein, without limitation, for purposes of convenience). The system 102 also generates 426 a mapping of the keywords to the template fields (referred to as "keyword to template mapping" herein, without limitation, for purposes of convenience). Through the keyword to template mapping, the system 102 may insert keywords detected in the uploaded data into the appropriate template fields.

In the exemplary embodiment described herein and still referring to FIG. 19, the system 102 generates 428 a mapping of the template fields to the instrument fields (referred to as "template to instrument mapping" herein, without limitation, for purposes of convenience). The template to instrument mapping includes a correspondence between the template fields and the instrument fields. In the embodiment of question A described above, question A corresponds to the following text: "please describe the severity of the pain you are experiencing." A particular instrument field (referred to as "instrument field A" herein, without limitation, for purposes of convenience) is associated with question A. In the illustrated embodiment, the system 102 associates a particular template field in the template (referred to as "template field A" herein, without limitation, for purposes of convenience) to correspond to instrument field A in the particular instrument including question A, thereby mapping instrument field A to template field A. The data filter module 127 may format the medical data (referred to as "formatted data values" herein, without limitation, for purposes of convenience) included in the template fields and insert the formatted data values into the appropriate instrument fields in the various instruments, using the template to instrument mapping to determine the correspondence between the instrument fields and the template fields.

Figure 20:
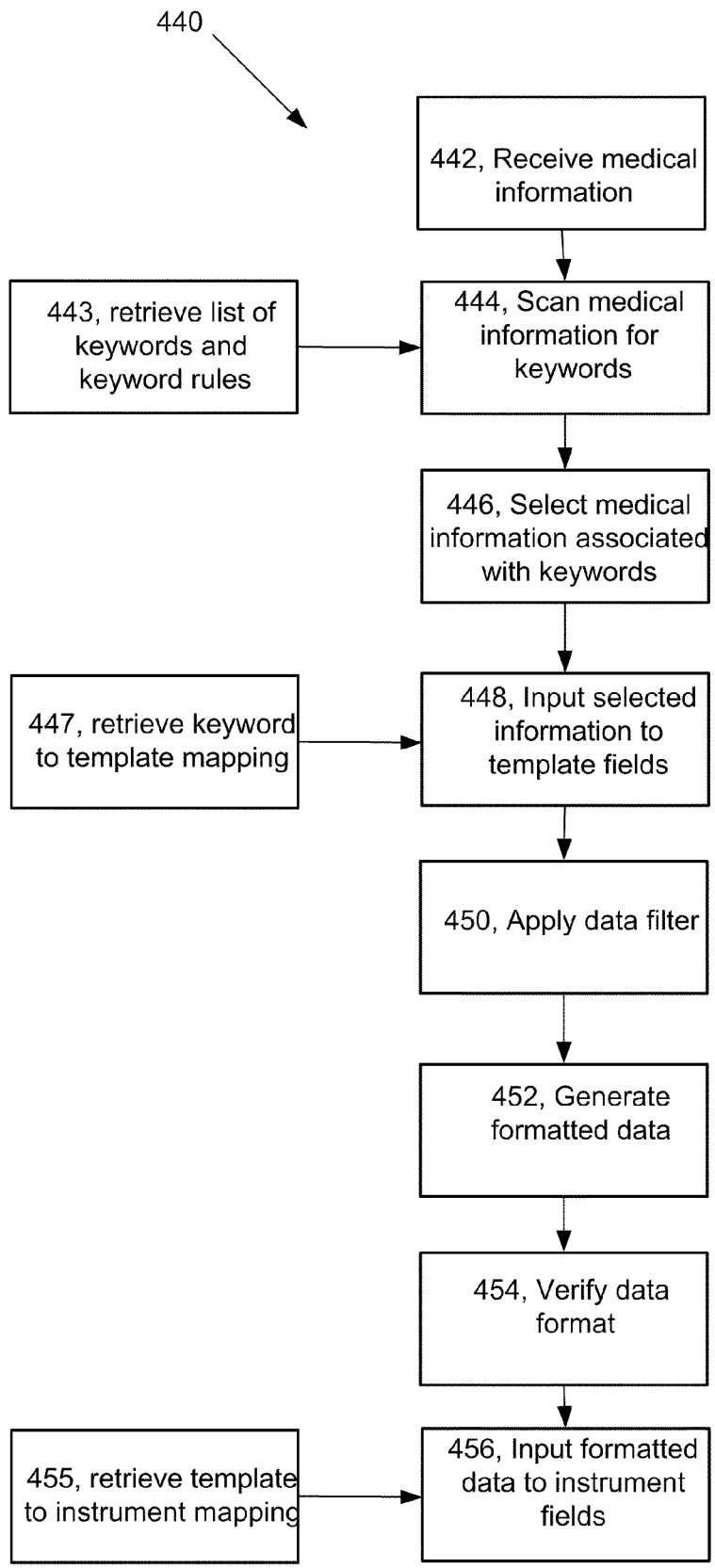

FIG. 20 illustrates a particular exemplary embodiment described herein. Referring to FIG. 20, the illustrated medical integration system 102 executes 440 and combines various processes including the following. In this exemplary embodiment, the system receives 442 the uploaded data from users of the system 102. The uploaded data may include medical data for many patients (e.g., the answers to medical assessment questions given to hundreds of patients). As used herein, the term "medical assessment question(s)" is understood to refer broadly, without limitation, to one or more questions used in classifying a medical condition and/or medical subject matter. The system 102 retrieves 443 the list of the keywords and the list of the keyword rules associated with the keywords. As used herein, the term "retrieve" refers broadly, without limitation, to any process or technique that makes available and/or locates and/or reads data from any type of data repository.

In the exemplary embodiment described herein, the system 102 applies the list of keywords and/or the keyword rules to the received, uploaded medical data and scans 444 the received, uploaded medical data for the keywords. When the system 102 detects a keyword in the uploaded data, the system 102 selects 446 medical data associated with the keyword. Referring to the exemplary embodiment of keyword A and question A described above, the text of keyword A corresponds to the question "please describe the severity of the pain you are experiencing." The system 102 applies keyword rule A, scans the uploaded medical data for keyword A and detects the presence of keyword A in the uploaded medical data. In this example, through the execution of keyword rule A, the system 102 selects, from the uploaded medical data, answer A, which in this particular embodiment corresponds to the following text: "I have been experiencing pain when I walk for the last 4 weeks."

In one embodiment, the system 102 retrieves 446 the keyword to template mapping to determine the appropriate field in the template in which to input the selected medical data. Through the application of and execution of the keyword to template mapping to the selected medical data, the system 102 may input 448 the selected medical data into the appropriate field in the template. The system 102 may also apply 450 the data filter module 127 to the uploaded data included in the template fields and generates 452 formatted data. The exemplary data filter module 127 includes rules and/or instructions to reformat the data included in the template fields according to the data format specifications (e.g., numerical formatting, alphanumerical formatting, special character formatting, and the like) associated with the appropriate instrument fields. In one particular embodiment and referring to question A described above, instrument field A specifies that data input into instrument field A should be formatted such that all numbers are written in an alphabetic format. In this embodiment, template field A includes the text of answer A, which may, for example, correspond to the following text: "I have been experiencing pain when I walk for the last 4 weeks." In this embodiment, the data filter module 127 reformats the text corresponding to answer A such that numbers are converted to alphabetical words and the text corresponding to answer A is reformatted as "I have been experiencing pain when I walk for the last four weeks." The reformatted text corresponding to answer A is then inserted from template field A into instrument field A.

In another embodiment where medical data is being uploaded for multiple patients (e.g., dozens or hundreds of patients), the system 102 scans 444 (e.g., simultaneous and/or iterative scanning) the uploaded data for each patient and groups together the medical data (e.g., across the multiple patients) associated with the same keyword. In one particular embodiment, medical data for patient A and patient B is received 442 by the system 102. The received medical data includes patient A's answer to question A and patient B's answer to question A. In this example, the system 102 scans 444 (e.g., through execution of the scanning tool) the received medical data and detects keyword A twice, because keyword A is included in the medical data associated with patient A and keyword A is also included in the medical data associated with patient B. Through the execution of keyword rule A, the system 102 selects 446 text corresponding to patient A's answer to question A and text corresponding to patient B's answer to question A (referred to as "answer B" herein, without limitation, for purposes of convenience) and inserts the text corresponding to answer A and answer B into template field A.

In the exemplary embodiment described herein, the data filter module 127 is applied 450 in a "batch mode" (e.g., processing a set of data at a time and/or in a single program run) to the text corresponding to answers A and B included in template field A, to generate formatted data for the text corresponding to answers A and B. In this embodiment, the formatted data for the text corresponding to answers A and B is inserted in batch into instrument field A. In one embodiment, the system 102 processes, receives and formats in real-time (e.g., iteratively and/or simultaneously) medical data for numerous and various patients (or medical studies, for example), using the template fields, instrument fields and template to instrument mapping.

In the illustrated embodiment, the system 102 verifies 454 that the formatted data in the template field comports to the data format specifications of the appropriate instrument fields. If the system 102 determines that the data in the template fields includes unformatted data, the system 102 may apply (e.g., iteratively) the data filter module 127 to the data included in the template fields.

In one embodiment, the system 102 retrieves 455 the template to instrument mapping and, through execution of and application of the template to instrument mapping to the data in the template fields, inputs 456 the formatted data into the appropriate instrument fields. The data may be stored in the data repository 126 and is capable of being mined and accessed by the research tools 120 as described above and herein.

In the exemplary embodiment described herein, a user of the system 102 uploads multiple years worth of medical data into the system 102 and through the use of the templates and the data filter module 127 reformats the uploaded data to comply with the data format specification of various instruments. Through the data reformatting, the data may be saved into the system 102 and accessed and mined by the research tools 120.

Instrument Selection Generator

Referring back to the illustrated example of FIG. 1, the medical integration system 102 may also include an instrument selection generator module 129. The illustrated instrument selection generator module 129 determines a collection of instruments to assign to a patient based on the patient's response to medical assessment questions. Based on the patient's response to these questions, the exemplary instrument selection generator module 129 applies a set of rules to the patient's responses. In the illustrated embodiment, the instrument selection generator module 129 determines the instruments that are appropriate for the patient to complete based on the patient's medical situation, as indicated by the patient's response to the medical assessment questions.

Figure 21:
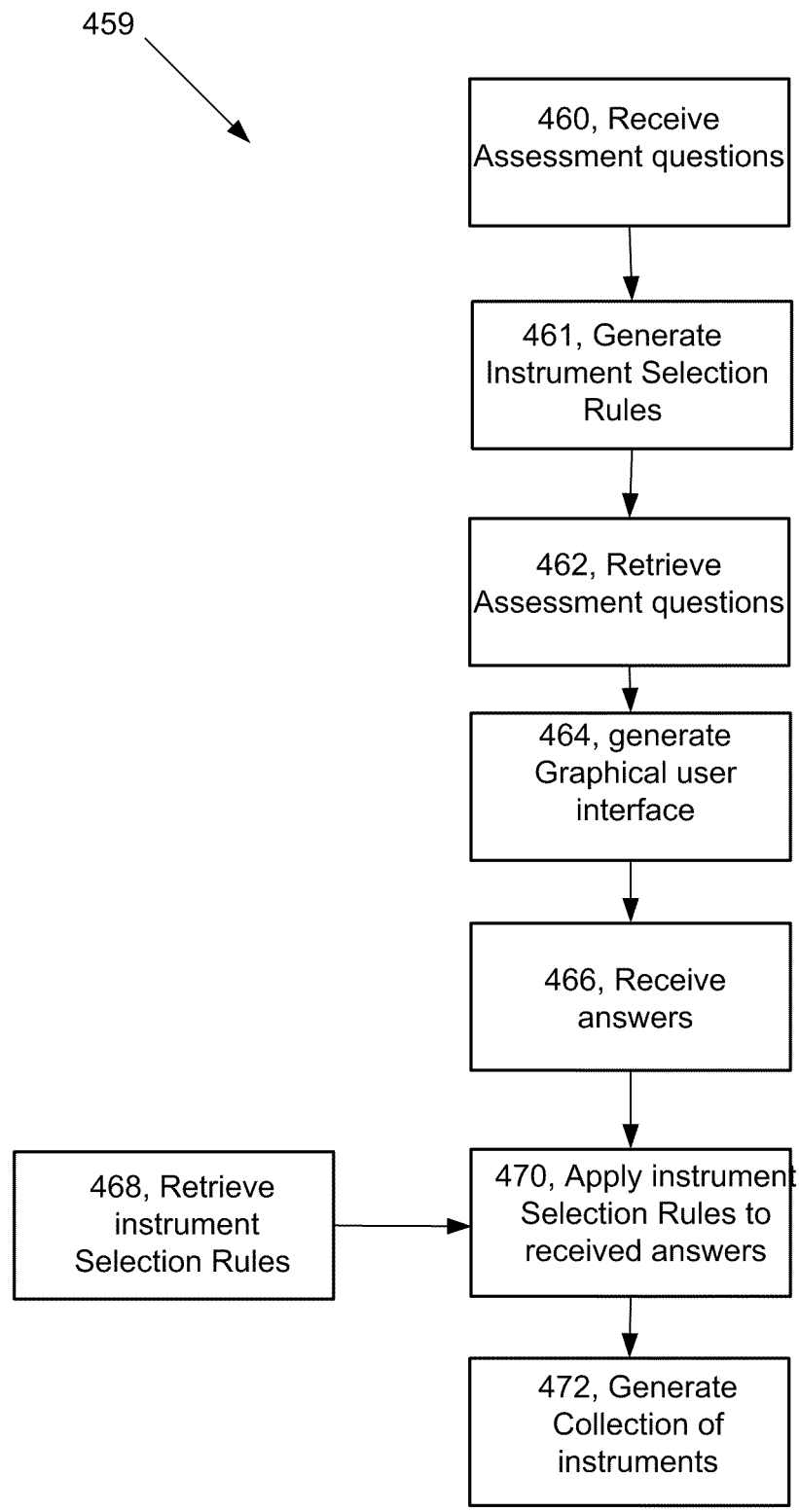

FIG. 21 illustrates a particular exemplary embodiment described herein. Referring to FIG. 21, the illustrated instrument selection generator module 129 executes 459 and combines various processes in generating a collection of instruments to present to a patient including the following. In the illustrated embodiment, the instrument selection generator module 129 receives 460 medical assessment questions from a user (e.g., a medical doctor) of the system 102. In one embodiment, the medical assessment questions include a series of questions pertaining to a known medical condition (e.g., a knee injury). In this exemplary embodiment, the medical assessment questions include the following series of questions:

Question 1: How are you feeling today?
Question 2: Do you have any pain?
Question 3: Do you have pain in your joints?
Question 4: Are you able to move around easily?
Question 5: Have you been well emotionally?
Question 6: Do you have trouble walking?
Question 7: Can you participate in sports?
Question 8: Do you have trouble sleeping?
Question 9: Are you able to squat?
Question 10: Can you do any heavy lifting?
Question 11: Are you able to walk uphill?

In the exemplary embodiment described herein, based on the received medical assessment questions, the instrument selection generator module 129 generates instrument selection rules. The exemplary instrument selection rules specify the instruments that are assigned to a patient based on the patient's responses to the medical assessment questions. In one particular embodiment and referring to Questions 1-11 described above, the instrument selection generator module 129 determines that if a patient answers yes to Questions 1, 3, 5, 6 and 7, then the patient is assigned Instrument 1 (e.g., an instrument pertaining to knee mobility), Instrument 2 (e.g., an instrument pertaining to knee pain) and Instrument 5 (e.g., an instrument pertaining to personal strength). If the patient's response to the medical assessment questions differs, then the assigned instruments may differ as well. In this particular embodiment, the instrument selection generator module 129 may determine that if a patient answers yes to Questions 1, 3, 5, 6, 7 and 10 that an additional instrument (e.g., Instrument 8 pertaining to overall strength and health) should also be assigned to the patient.

In one embodiment, the instrument selection generator module 129 determines the instruments to assign to a patient based on a mapping of the medical assessment questions to the various instruments (referred to as "question to instrument mapping" herein, without limitation, for the purposes of convenience). In this embodiment, the question to instrument mapping may specify that Questions 1, 2 and 3 pertain to pain and if a patient answers yes to Questions 1, 2 and/or 3 that Instrument 2 should be assigned to the patient.

In another embodiment, the question to instrument mapping is generated by a user inputting into the system 102 a list of a series of the medical assessment questions and instruments corresponding to the medical assessment questions. In yet another embodiment, the instrument selection generator module 129 generates the question to instrument mapping by scanning the medical assessment questions for phrases, words, characters and/or sentences (collectively referred to as "phrases" herein, without limitation, for purposes of convenience) that are the same and/or similar to phrases included in the various instruments stored in the database 126. When the exemplary instrument selection generator module 129 determines a phrase in a medical assessment question that is similar to (and/or the same as) a phrase in an instrument, the instrument selection generator module 129 may generate a rule that when a patient answers affirmatively (e.g., yes) to the medical assessment question that the instrument (including the same and/or similar phrase) is assigned to the patient.

In the exemplary embodiment described herein, the instrument selection generator module 129 retrieves 462 the medical assessment questions and generates 464 a graphical user interface that when rendered on a display device renders a visual representation of the medical assessment questions on the display device for the patient. In this embodiment, the instrument selection generator module 129 receives 466 answers to the medical assessment questions, retrieves 468 the instrument selection rules and applies 470 the instrument selection rules to the received answers. In the illustrated embodiment, using the techniques described above, the instrument selection generator module 129 generates 472 a collection of instruments and assigns the collection of instruments to the patient, based on the application of the instrument selection rules to the received answers.

Medical Interactive Slate

Referring back to the illustrated example of FIG. 1, the illustrated medical integration system 102 may also include a medical interactive slate ("MIS") module 125. The illustrated MIS module 125 generates a summation of a patient's medical data during a patient's stay in a medical facility (e.g., a clinic or a hospital). The exemplary MIS module 125 analyzes in real-time the patient's medical data while the patient is in the medical facility and integrates in real-time this medical data with the patient's history from previous visits.

Figure 22:
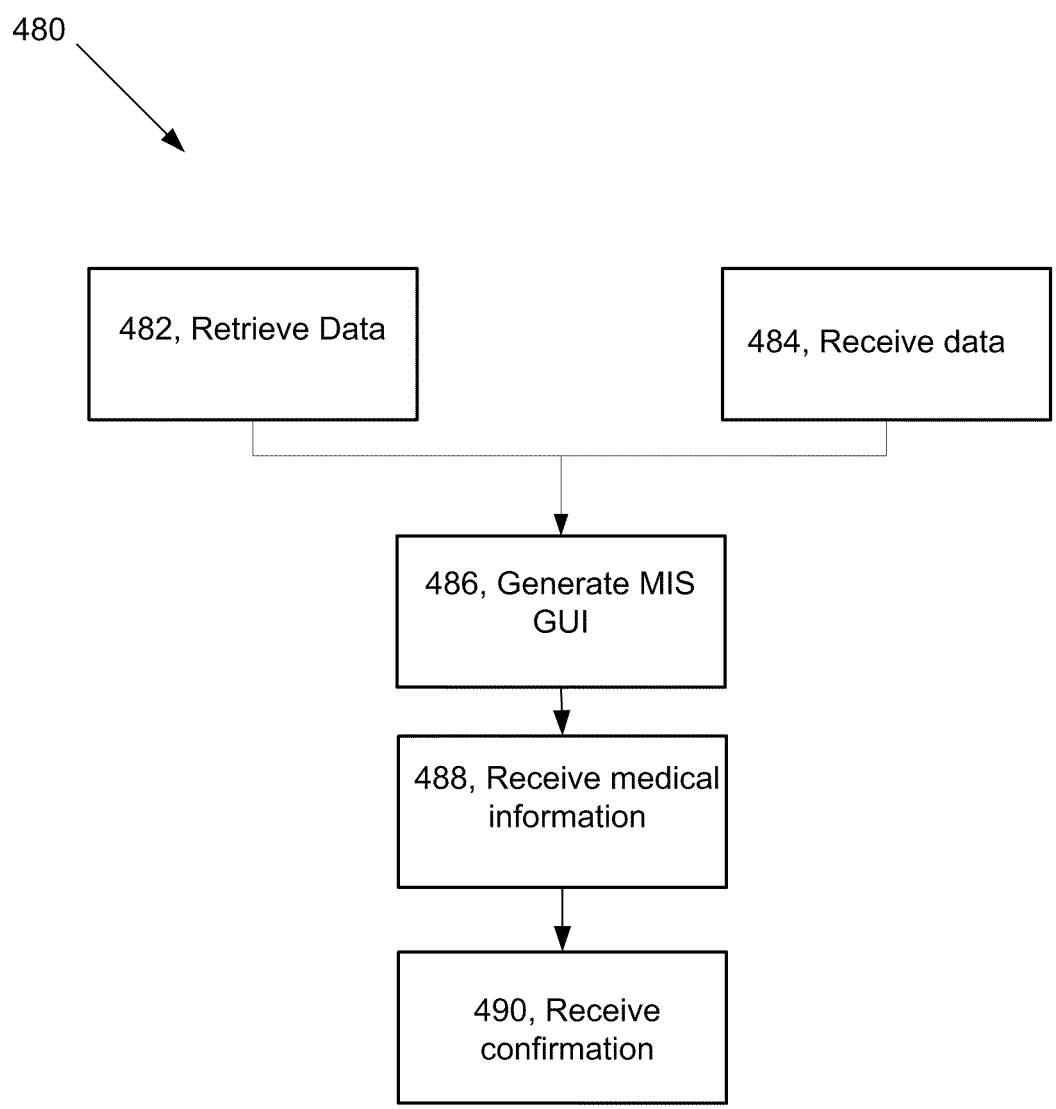

FIG. 22 illustrates a particular exemplary embodiment described herein. Referring to FIG. 22, the illustrated MIS module 125 executes 480 and combines various processes in generating the medical interactive slate graphical user interface. The exemplary MIS module 125 collects information pertaining to a patient or other user of the system 102, for example, by retrieving 482 medical data stored by the system 102 in the databases 126 (e.g., medical data collected from a patient's answers to an instrument completed prior to the patient's medical visit). In the illustrated embodiment, the MIS module 125 also collects information pertaining to the patient, for example, by receiving 484 medical data from the patient during the visit (e.g., collecting medical data from a patient based on the patient's answers to questions in an instrument completed during the patient's visit to the medical facility).

In the exemplary embodiment described herein, the MIS module 125 generates a MIS graphical user interface based on the retrieved and the received medical data, as discussed in further detail below. In one embodiment, as the patient is examined by a health care professional (e.g., a nurse and a physician), the health care professional enters notes about the current condition of the patient and the MIS module 125 receives 488 the entered information. Through the MIS graphical user interface, the health care professional also views the patient's medical data. In one embodiment, the notes and entered medical data are sent to the EMR system 128 for storage. In the illustrated embodiment, the system 102 receives 490 confirmation of a patient's medical data (e.g., medical status, diagnoses, and the like) from the health care professional, for example, when there has been no or relatively minor changes in the patient's status and/or medical data, as described in further detail below.

Figure 23:
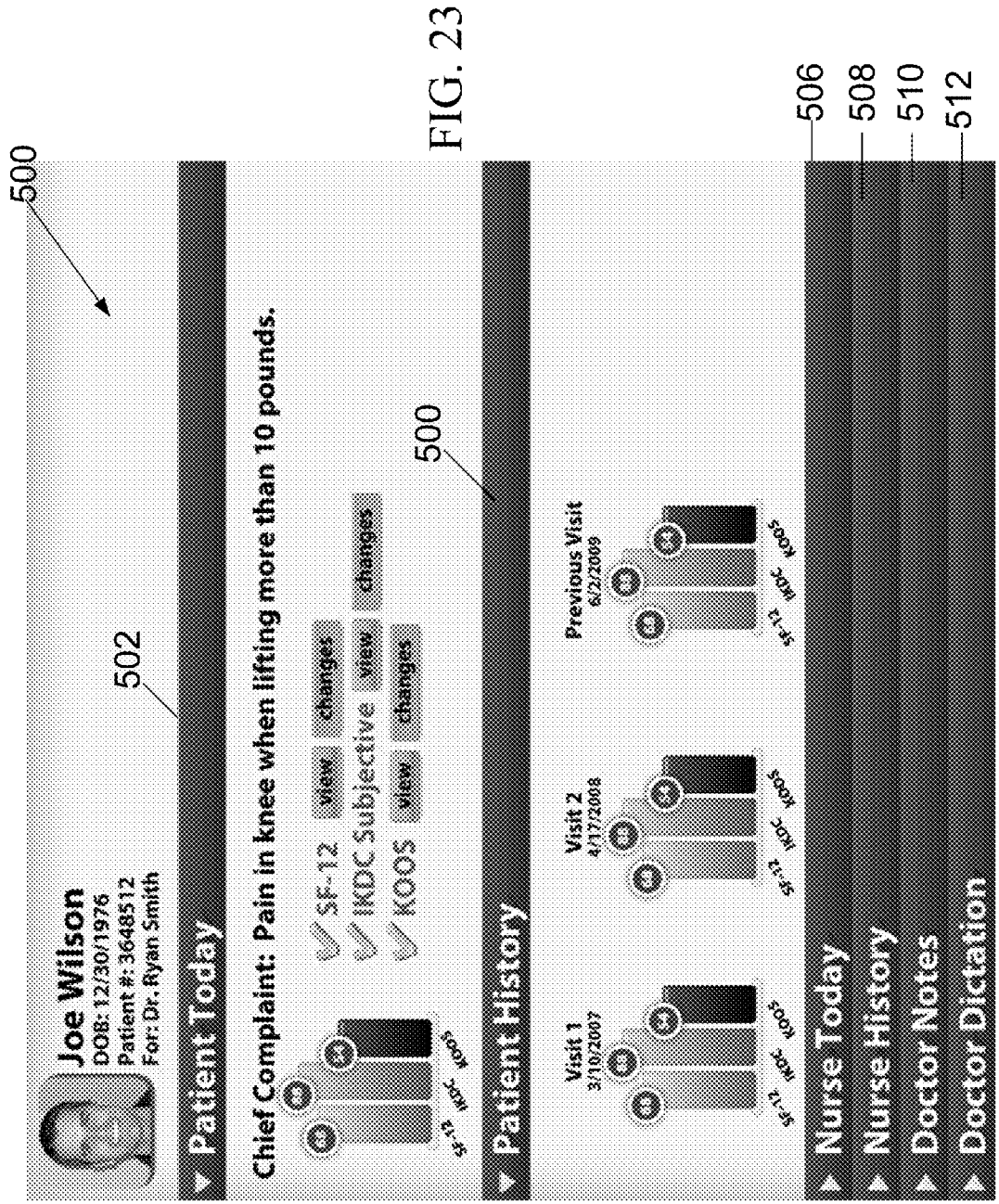

FIG. 23 illustrates a particular exemplary embodiment described herein. Referring to FIG. 23, the illustrated MIS graphical user interface 500 includes a section 502, with visual representations of the patient's current medical data, and a section 504, with visual representations of the patient's medical data associated with previous visits. In the illustrated embodiment, the MIS graphical user interface 500 also includes sections 506, 508 for a nurse or other health care professional to add notes or to otherwise supplement the patient's medical data. The exemplary MIS graphical user interface 500 also includes sections 510, 512 for a physician or other health care professional to add notes or to otherwise supplement the patient's health history.

Figure 24:
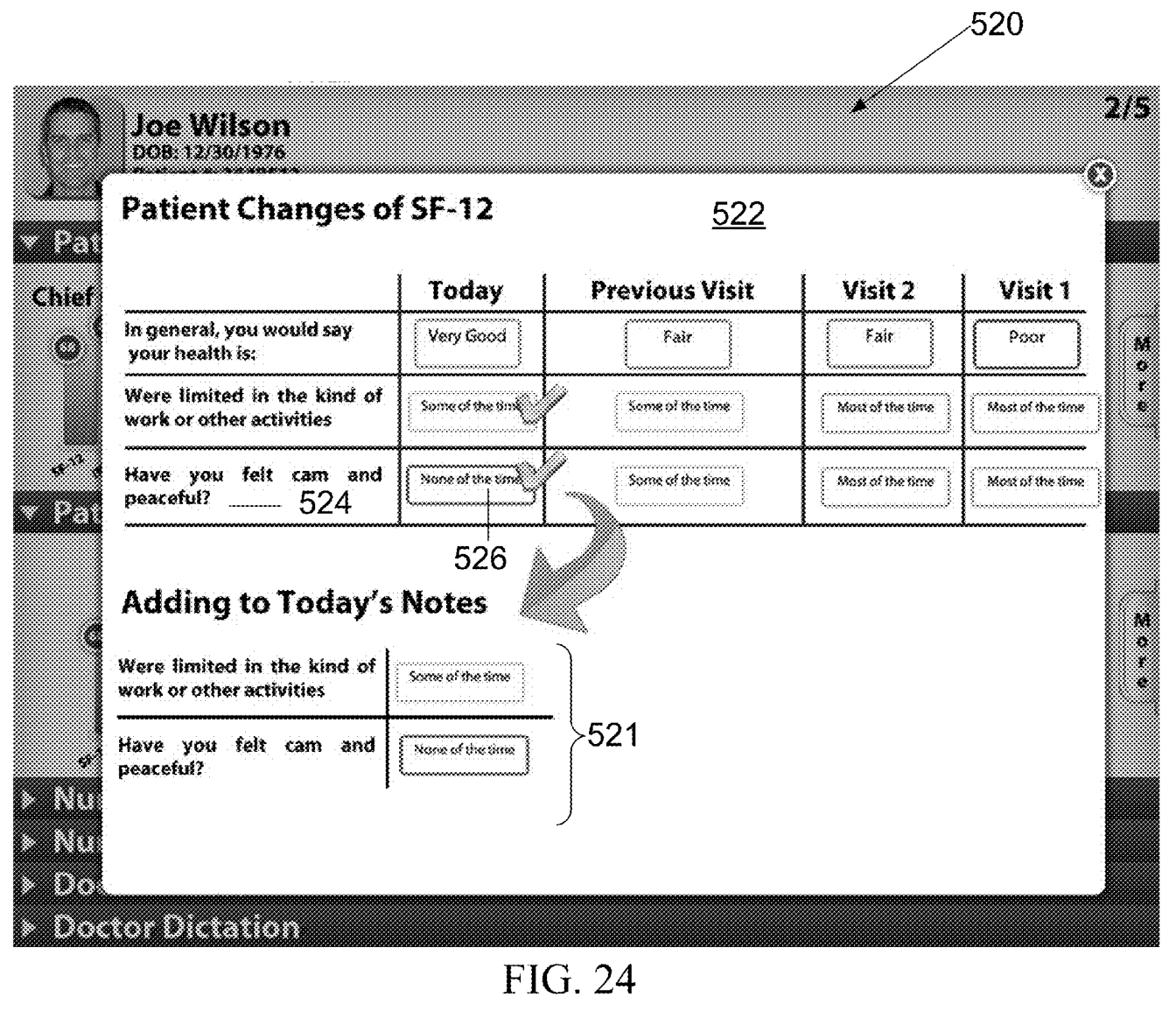

FIG. 24 illustrates a particular exemplary embodiment described herein. Referring to FIG. 24, the illustrated MIS graphical user interface 520 includes a section 522 in which a patient's current medical data may be updated with additional new medical data. As used herein, the term "update" refers broadly to any type of process or technique that adds and/or deletes any type of data to and/or from any type of data repository, including, for example, the creation of a new database record for a patient. In the illustrated embodiment, section 524 includes a visual representation of a question included in an instrument. In this exemplary embodiment, link 526 is juxtaposed to section 524 and link 526 corresponds to the visual representation of the answer to the question corresponding to section 512. As used herein, the term "juxtapose" refers broadly to the position of any type of data item in relation to another data item of any type. The answer to the question associated with section 524 may be changed, for example, by selecting link 526, selection of which causes a dialog box or a drop down box (not shown) to display textual representations of answers corresponding to the question associated with exemplary section 524. In one embodiment, the textual representations of answers corresponding to the question are associated with a pointer that is associated with a database entry corresponding to the patient's medical record, so that when a new answer is selected for the question the database entry may be updated with the new information.

In this embodiment, when the physician (or other user) selects a new answer, a computing device 110 (FIG. 1) associated with the physician generates an update message including data indicative of the text corresponding to the new answer. The illustrated computing device 110 associated with the physician sends the update message to the system 102 and the system 102 receives the update message. In another embodiment, the selection of a new answer (e.g., by a nurse, physician or other health care professional) causes the system 102 to create a new database entry in the illustrated database 126 and insert the new answer and the corresponding question into the newly inserted database entry. In the illustrated embodiment, section 521 of the graphical user interface includes a visual representation of medical data that has been updated (e.g., by a nurse or other health care professional) for the patient.

Figure 25:
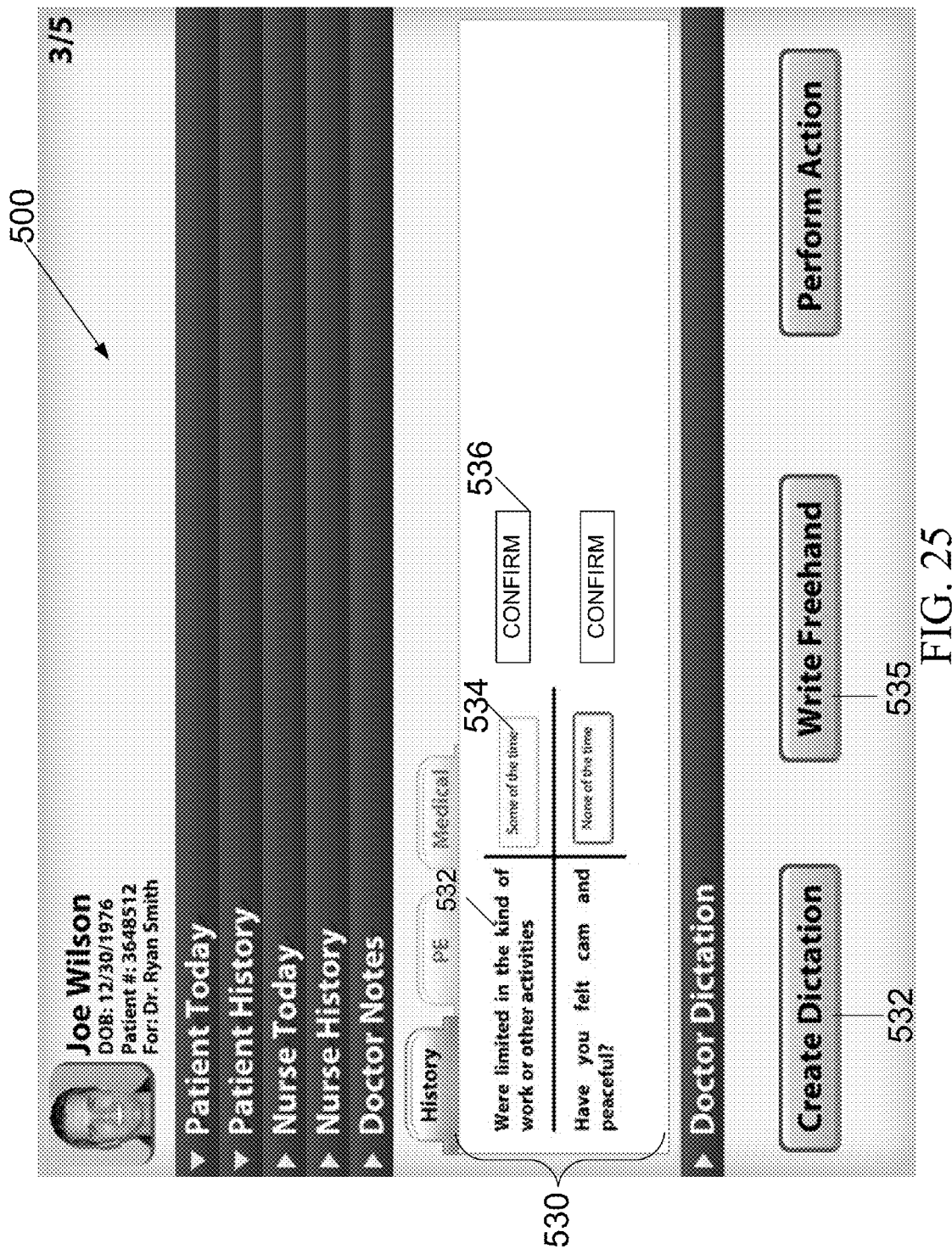

FIG. 25 illustrates a particular exemplary embodiment described herein. Referring to FIG. 25, section 530 of the MIS graphical user interface 500 provides a visual representation of portions of the patient's medical data. In the illustrated embodiment, section 530 includes a visual representation 532 of the text of a question for which the patient has supplied an updated answer. Section 534 may also include a visual representation of the patient's updated answer for the question. In one embodiment, section 534 also includes a selectable field (e.g., a link, a button, a selectable area, and the like) selection of which enables a physician (or any other health care professional) to update the patient's answer to the question associated with section 532. In one particular embodiment, the patient may have provided a nurse with an incorrect answer during an initial triage session and the patient recognizes this answer as incorrect. In this embodiment, section 534 enables the physician to correct the patient's prior answer. Through selection of the selectable field in section 534, the physician may update the patient's answer (for example by inserting text in a text field associated with section 534 or through selection of a new response that is provided in a drop down menu of possible response). In the illustrated example, the selectable field in section 534 is associated with a pointer that links to the appropriate database entry (e.g., corresponding to the patient's medical record) in the database 126. Through the pointer, the value of the patient's answer may be updated in the database 126, without having to replicate data (e.g., adding a new database entry including the question and the patient's updated answer).

In the exemplary embodiment described herein, the patient's answer to the particular question represented in section 532 may be correct and does not need to be updated. In this embodiment, the MIS graphical user interface displays a visual representation of a "confirmation" section (e.g., a button, a link, a selectable area, and the like) 536. The physician selects the confirmation section 536 to "confirm" that the medical data entered by the nurse (or other health care professional) is accurate. In one embodiment, the physician's selection of the confirmation section 536 causes a computing device 110 (FIG. 1) being used by the physician to generate a confirmation message (e.g., a message including data indicating that the physician has reviewed the patient's medical data). The illustrated computing device 110 sends the confirmation message to the system 102 and the system 102 receives the confirmation message.

In another embodiment, through selection of the confirmation section 536 and receipt of a confirmation message by the system 102, the database entry corresponding to the patient's medical record is updated with information indicating that the physician (or other health care professional) has reviewed and confirmed the updated record and medical data associated with the patient. In yet another embodiment, through selection of the confirmation section 536, the physician reviews the information that has already been entered by the nurse or that is already part of the patient's medical history (e.g., medical data that the patient previously submitted to the system 102 through the patient's completion of an instrument) and confirms that this information is correct and accurate, without generating a new database entry and duplicating medical data that has already been entered into the system.

In the illustrated embodiment, section 512 also includes links 532, 535, selection of which allows a health care professional to add dictation notes to the database entry corresponding to the patient's medical record, as discussed in further detail below. In one embodiment, when a health care professional adds dictation notes through a dictation notes field 550 (FIG. 27) and 544 (FIG. 26), the database entry corresponding to the patient's medical record is updated in real-time and through a pointer associated with the dictation notes field 550 (FIG. 27) and 544 (FIG. 26).

Figure 26:

FIG. 26 illustrates a particular exemplary embodiment described herein. Referring to FIG. 26, an exemplary dialog box 540 (which may be displayed, for example, upon selection of link 532 (FIG. 25)) enables a health care professional to add dictation notes to a patient's medical record. Dialog box 540 includes link 542, selection of which causes a microphone (not shown) to start recording the words a health care professional is speaking into the microphone. In the illustrated embodiment, dialog box 540 includes text box 544, which displays a visual representation of the words spoken by the health care professional.

Figure 27:
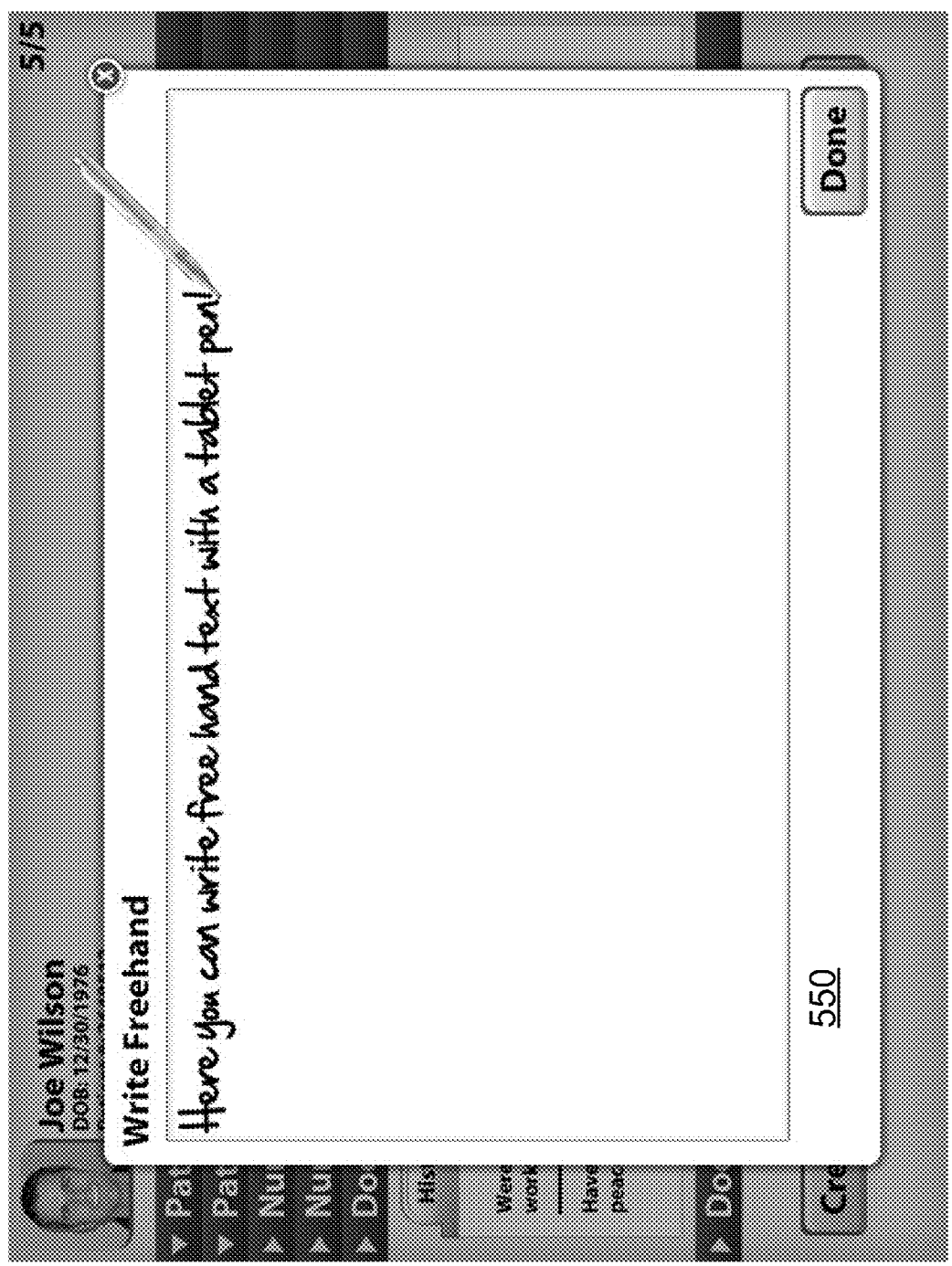

FIG. 27 illustrates a particular exemplary embodiment described herein. Referring to FIG. 27, an exemplary dialog box 550 (which may be displayed, for example, upon selection of link 535 (FIG. 25)) enables a health care professional to add dictation notes to a patient's medical record by hand, for example, through the use of a tablet pen. In one embodiment, using a tablet pen, for example, a health care professional enters notes in the form of text into the dialog box 550. Through a pointer, the system 102 may associate the entered text with the patient's medical record in the database 126 and store the entered text in database 126.

As used herein, the terms "computer" and "computer systems" refer broadly to any sort of combination of one or more servers and/or computing devices. As used herein, the terms "instrument(s)" and "medical study instrument(s)" refer broadly to any type of device and/or document (or any combination thereof), which presents data and/or information to a user and allows the user to input and/or send data and/or information to the system 102

Embodiments can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., a LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back end component, e.g., as a data server, or that includes a middleware component, e.g., an application server, or that includes a front end component, e.g., a client computer having a graphical user interface or a Web browser through which a user can interact with an implementation of embodiments, or any combination of such back end, middleware, or front end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be information in different formats such as text, graphics, images, sound, video, Hypertext Markup Language (HTML), as well as programs. Upon specification of a link by the user, the client computer makes a TCP/IP request to a Web server and receives information, which may be another Web page that is formatted according to HTML. Users can also access other pages on the same or other servers by following instructions on the screen, entering certain data, or clicking on selected icons. It should also be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view information available on servers or networks on the Web through the use of browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

Other embodiments are within the scope and spirit of the description claims. In one embodiment, the rules described herein (e.g., the procedure determination rules or the medical assessment rules) are executed by a rules engine included in the system 102. In another embodiment, data collected by the system 102 through the instruments is stored in an EMR system 128. The research tool may then query the EMR system 128 for patient data matching one or more patient criteria. Through the network 112, the matching data is returned to the system 102 and the research tool processes and analyzes the returned data. In yet another embodiment, the techniques described herein are used to generate, review and validate instruments pertaining to various fields (e.g., the veterinary field, the legal field and the financial services field) and collect and retrieve data for the instruments pertaining to the various fields. In still another embodiment, the instrument generation module 116, the instrument validation module 118, the research tools module 120, the procedure determination module 122 and the patient flow module 124 are integrated together through various communication channels and/or are implemented as an instrument generation system, an instrument validation system, a research tools system, a procedure determination system and a patient flow system (collectively referred to as "the systems" herein, without limitation, for the purposes of convenience), with each system including one or more servers or computing devices and the systems being integrated together through various communication channels and/or network connections.

Additionally, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the invention. Accordingly, other embodiments are within the scope of the following claims.

What is claimed is:
1. A computer-implemented method comprises:
transmitting, to a device used by a physician, information for a graphical user interface for enabling the physician to define custom medical assessment questions for a customized medical study instrument of the physician, wherein rendering of the graphical user interface on the device used by the physician displays:
a first portion for the physician to select a type of question to be added to the medical study instrument; and
a second portion for the physician to enter text associated with the question;
receiving, from the device used by the physician in response to transmittal of the information for the graphical user interface, request messages including data indicative of custom questions to be included in the medical study instrument of the physician;
generating, based on the request messages, the customized medical study instrument of the physician;
associating a particular custom medical assessment question with an alert feature for causing the physician to be notified of an answer to the particular custom medical assessment questions;
receiving, from device used by the physician, an answer threshold value for the particular custom medical assessment question, with the answer threshold value specifying a range of values that causes the one or more computer systems to execute the alert feature;
receiving from a patient, through one or more computer systems, one or more responses to one or more instrument selection questions;
assigning the customized medical study instrument of the physician to the patient, with assigning based on the one or more responses of the patient to the one or more instrument selection questions;
receiving, from the patient, answers to the custom medical assessment questions for the customized medical study instrument of the physician;
detecting that a value in the answer to the particular custom medical assessment question associated with the alert feature exceeds the answer threshold value;
generating, in response to detecting based on the alert feature, a notification message to alert the physician that the patient has answered the particular custom medical assessment question with the value that exceeds the answer threshold value, wherein the notification message differs from the alert feature; and
sending, to the device used by the physician, the notification message for display in a dashboard graphical user interface for providing the physician with a view of the particular custom medical assessment question and the value that exceeds the answer threshold value.

2. The computer-implemented method of claim 1 further comprising:

generating one or more instrument selection rules, with the one or more instrument selection rules indicating a correspondence between the one or more responses to the one or more instrument selection questions and medical study instruments.

3. The computer-implemented method of claim 1 further comprising:

applying the one or more instrument selection rules to the one or more responses to the one or more instrument selection questions; and generating, based on application of the one or more instrument selection rules to the one or more responses, a list of medical study instruments to be associated with the patient, with the list including the customized medical study instrument of the physician.

4. A computer program product embodied on a computer readable storage medium, the computer program product comprising instructions for causing a computer to perform operations comprising:

transmitting, to a device used by a physician, information for a graphical user interface for enabling the physician to define custom medical assessment questions for a customized medical study instrument of the physician, wherein rendering of the graphical user interface on the device used by the physician displays:

a first portion for the physician to select a type of question to be added to the medical study instrument; and a second portion for the physician to enter text associated with the question;

receiving, from the device used by the physician in response to transmittal of the information for the graphical user interface, request messages including data indicative of custom questions to be included in the medical study instrument of the physician;

generating, based on the request messages, the customized medical study instrument of the physician;

associating a particular custom medical assessment question with an alert feature for causing the physician to be notified of an answer to the particular custom medical assessment questions;

receiving, from device used by the physician, an answer threshold value for the particular custom medical assessment question, with the answer threshold value specifying a range of values that causes the one or more computer systems to execute the alert feature;

receiving from a patient, through one or more computer systems, one or more responses to one or more instrument selection questions;

assigning the customized medical study instrument of the physician to the patient, with assigning based on the one or more responses of the patient to the one or more instrument selection questions;

receiving, from the patient, answers to the custom medical assessment questions for the customized medical study instrument of the physician;

detecting that a value in the answer to the particular custom medical assessment question associated with the alert feature exceeds the answer threshold value;

generating, in response to detecting based on the alert feature, a notification message to alert the physician that the patient has answered the particular custom medical assessment question with the value that exceeds the answer threshold value, wherein the notification message differs from the alert feature; and sending, to the device used by the physician, the notification message for display in a dashboard graphical user interface for providing the physician with a view of the particular custom medical assessment question and the value that exceeds the answer threshold value.

5. The computer program product of claim 4, wherein the operations further comprise:

generating one or more instrument selection rules, with the one or more instrument selection rules indicating a correspondence between the one or more responses to the one or more instrument selection questions and medical study instruments.

6. The computer program product of claim 4, wherein the operations further comprise:

applying the one or more instrument selection rules to the one or more responses to the one or more instrument selection questions; and generating, based on application of the one or more instrument selection rules to the one or more responses, a list of medical study instruments to be associated with the patient, with the list including the customized medical study instrument of the physician.

7. An apparatus comprising:

a processor; and a computer program product embodied on a computer readable storage medium, the computer program product comprising instructions for causing the processor to perform operations comprising:

transmitting, to a device used by a physician, information for a graphical user interface for enabling the physician to define custom medical assessment questions for a customized medical study instrument of the physician, wherein rendering of the graphical user interface on the device used by the physician displays:

a first portion for the physician to select a type of question to be added to the medical study instrument; and a second portion for the physician to enter text associated with the question;

receiving, from the device used by the physician in response to transmittal of the information for the graphical user interface, request messages including data indicative of custom questions to be included in the medical study instrument of the physician;

generating, based on the request messages, the customized medical study instrument of the physician;

associating a particular custom medical assessment question with an alert feature for causing the physician to be notified of an answer to the particular custom medical assessment questions;

receiving, from device used by the physician, an answer threshold value for the particular custom medical assessment question, with the answer threshold value specifying a range of values that causes the one or more computer systems to execute the alert feature;

receiving from a patient, through one or more computer systems, one or more responses to one or more instrument selection questions;

assigning the customized medical study instrument of the physician to the patient, with assigning based on the one or more responses of the patient to the one or more instrument selection questions;

receiving, from the patient, answers to the custom medical assessment questions for the customized medical study instrument of the physician;

detecting that a value in the answer to the particular custom medical assessment question associated with the alert feature exceeds the answer threshold value;

generating, in response to detecting based on the alert feature, a notification message to alert the physician that the patient has answered the particular custom medical assessment question with the value that exceeds the answer threshold value, wherein the notification message differs from the alert feature; and sending, to the device used by the physician, the notification message for display in a dashboard graphical user interface for providing the physician with a view of the particular custom medical assessment question and the value that exceeds the answer threshold value.

8. The apparatus of claim 7, wherein the operations further comprise:

generating one or more instrument selection rules, with the one or more instrument selection rules indicating a correspondence between the one or more responses to the one or more instrument selection questions and medical study instruments.

9. The apparatus of claim 7, wherein the operations further comprise:

applying the one or more instrument selection rules to the one or more responses to the one or more instrument selection questions; and generating, based on application of the one or more instrument selection rules to the one or more responses, a list of medical study instruments to be associated with the patient, with the list including the customized medical study instrument of the physician.

10. The computer-implemented method of claim 1 further comprising:

retrieving from the one or more computer systems the one or more instrument selection questions.

11. The computer-implemented method of claim 1, further comprising:

generating, from the answers, de-identified data by removing from the answers information that identifies the patient;

generating an encrypted identifier that is associated with the patient;

generating an association between the de-identified data and the encrypted identifier; and providing the encrypted identifier to the physician to enable the physician to access fields in the medical study instrument that the physician has permission to access.

12. The computer-implemented method of claim 1, wherein the custom medical assessment questions in the customized medical study instrument of the physician relate to an efficacy of a medical device.

13. The computer-implemented method of claim 1, wherein the custom medical assessment questions in the customized medical study instrument of the physician relate to an efficacy of a medical technique.

14. The apparatus of claim 7, wherein the operations further comprise:

generating, from the answers, de-identified data by removing from the answers information that identifies the patient;

generating an encrypted identifier that is associated with the patient;

generating an association between the de-identified data and the encrypted identifier; and providing the encrypted identifier to the physician to enable the physician to access fields in the medical study instrument that the physician has permission to access.

15. The apparatus of claim 7, wherein the custom medical assessment questions in the customized medical study instrument of the physician relate to an efficacy of a medical device.

16. The apparatus of claim 7, wherein the custom medical assessment questions in the customized medical study instrument of the physician relate to an efficacy of a medical technique.

17. The computer program product of claim 4, wherein the operations further comprise:

generating, from the answers, de-identified data by removing from the answers information that identifies the patient;

generating an encrypted identifier that is associated with the patient;

generating an association between the de-identified data and the encrypted identifier; and providing the encrypted identifier to the physician to enable the physician to access fields in the medical study instrument that the physician has permission to access.

18. The computer program product of claim 4, wherein the custom medical assessment questions in the customized medical study instrument of the physician relate to an efficacy of a medical device.

19. The computer program product of claim 4, wherein the custom medical assessment questions in the customized medical study instrument of the physician relate to an efficacy of a medical technique.

* * * * *